(12) United States Patent
Webb et al.

(10) Patent No.: US 7,332,328 B2
(45) Date of Patent: *Feb. 19, 2008

(54) MICROCOLUMN-PLATFORM BASED ARRAY FOR HIGH-THROUGHPUT ANALYSIS

(75) Inventors: Brian L. Webb, Painted Post, NY (US); Jinlin Peng, Painted Post, NY (US); Michael D. Brady, Painted Post, NY (US); Mircea Despa, Horseheads, NY (US); Keith A. Horn, Corning, NY (US); Joydeep Lahiri, Painted Post, NY (US); David M. Root, Westford, MA (US); James B. Stamatoff, Painted Post, NY (US); Po Ki Yuen, Corning, NY (US)

(73) Assignee: Corning Incorporated, Corning, NY (US)

( * ) Notice: Subject to any disclaimer, the term of this patent is extended or adjusted under 35 U.S.C. 154(b) by 516 days.

This patent is subject to a terminal disclaimer.

(21) Appl. No.: 10/236,120

(22) Filed: Sep. 6, 2002

(65) Prior Publication Data

US 2003/0124029 A1    Jul. 3, 2003

Related U.S. Application Data

(60) Provisional application No. 60/317,660, filed on Sep. 7, 2001.

(51) Int. Cl.
*C12M 1/34* (2006.01)

(52) U.S. Cl. .................. 435/287.2; 435/288.3

(58) Field of Classification Search ...... None
See application file for complete search history.

(56) References Cited

U.S. PATENT DOCUMENTS

| 5,772,967 | A | 6/1998 | Wannlund et al. ......... 422/102 |
| 5,795,748 | A | 8/1998 | Cottingham ............... 435/91.2 |
| 6,022,700 | A | 2/2000 | Monks et al. ................ 435/30 |
| 6,396,995 | B1* | 5/2002 | Stuelpnagel et al. ........ 385/136 |
| 6,905,816 | B2* | 6/2005 | Jacobs et al. .................. 435/5 |
| 2001/0006417 | A1 | 7/2001 | Modlin et al. .............. 356/246 |

FOREIGN PATENT DOCUMENTS

| DE | 19541980 A1 | 4/1996 |
| EP | 0 709 678 | 5/1996 |
| EP | 0 709 678 | 1/2001 |
| WO | 93/09872 | 5/1993 |
| WO | WO 93/09872 | 5/1993 |
| WO | WO 98 29736 | 7/1998 |
| WO | WO 99 00657 | 1/1999 |
| WO | 00/39587 | 7/2000 |
| WO | WO 00/39587 | 7/2000 |
| WO | WO 00 71992 | 11/2000 |
| WO | WO 01 62378 | 8/2001 |
| WO | 02/42775 | 5/2002 |
| WO | WO 02/42775 | 5/2002 |

* cited by examiner

*Primary Examiner*—David Redding
(74) *Attorney, Agent, or Firm*—Tina N. Thompson; Thomas R. Beall

(57) ABSTRACT

A device and methods for performing biological or chemical analysis is provided. The device includes an array of three-dimensional microcolumns projecting away from a support plate. Each microcolumn has a relatively planar, first surface remote from the support plate. An array of multiple, different biological materials may be attached to the first surface. The device, when used in combination with existent micro-titer well plates, can improve efficiency of binding assays using microarrays for high-throughput capacity.

22 Claims, 27 Drawing Sheets

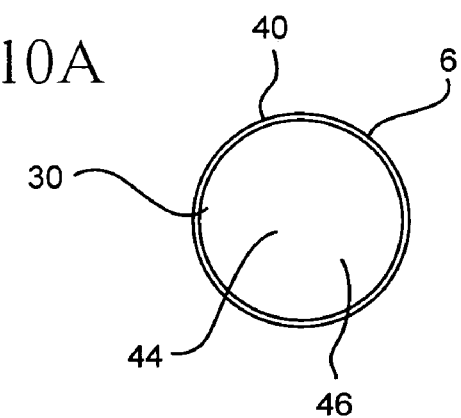
FIG. 10A
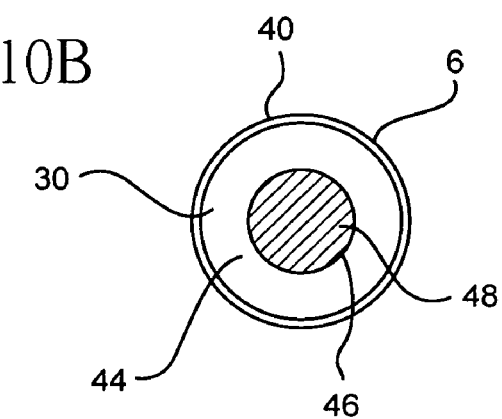
FIG. 10B
FIG. 10C
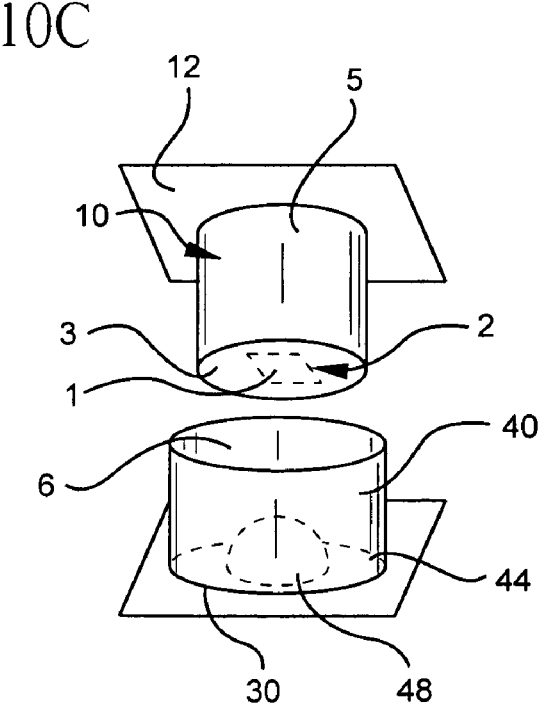

DUPLICATES 1X 30 μL

1 X 9 μL 1X 9 μL
WITH
MICROCOLUMN 3X 9 μL
WITH
MICROCOLUMN

MICROCOLUMN-PLATFORM BASED ARRAY FOR HIGH-THROUGHPUT ANALYSIS

CLAIM OF PRIORITY

The present Application claims priority to U.S. Provisional Application No. 60/317,660, filed on Sep. 7, 2001, in the name of Michael D. Brady et al., the content of which is incorporated herein by reference.

FIELD OF TECHNOLOGY

The present invention relates to an apparatus and method for biological analysis. In particular, the invention pertains to arrays of three-dimensional elevated surfaces, which may be used in combination with existent micro-titer well plates for performing high-throughput assays or other biological experiments.

BACKGROUND

The proliferation of biological targets and candidate drug compounds in high-throughput screening and the increased interest in characterizing the human genome have created a high demand for rapid, efficient, and reproducible study of many genes and the proteins for which they encode. Fundamental constraints such as time or limited quantities of samples can affect the efficiency of analysis. Current devices, although accurate and sensitive, are not conducive to the simultaneous, high-volume processing of many different assays of different experimental reagents or conditions in a single device.

At present, microarrays—also known as "DNA chips"—have emerged as a powerful tool for studying thousands of genes simultaneously in a single experiment. DNA-array technology has broad applications in genomic and pharmaceutical research, as well as medical diagnostics, which include gene discovery, gene expression monitoring, polymorphism screening, drug discovery, and clinical trial monitoring. The initial format of DNA arrays has been a glass slide or nylon filter containing about 100 to about 60,000 genes per slide. These microarrays have focused on mass processing of large numbers of samples under one experimental condition. This format permits analysis of many genes per sample, but unfortunately has not been conducive for high throughput analysis of many different samples under different, parallel assay conditions.

A second device is the multi-well plate—also known as micro-titer plates. Currently the most popular format for high throughput analysis of biological samples, the multi-well plate format has been standardized in the industry, and is machine friendly or compatible with robotic automation. The multi-well format enables researchers to process samples in parallel under many different experimental conditions, but has been limited in the relatively low numbers of samples per well. In the past, practical considerations, such as sample size, labor costs, and analysis time, placed limits on the use of multi-well plates for multiplexed analysis. Typically, only a single kind of surface-bound molecule is immobilized per well for binding assays. in an individual multi-well plate only one reading per well can be taken. This of course, limits the amount of information that can be gathered per unit of sample.

In view of the virtues of these two formats, however, considerable interest has arisen for smaller "thematic" arrays of selective nucleic sequences. Some kinds of thematic arrays are printed on the bottoms of wells in multi-well plates, so as to generate multiple arrays of nucleic sequences with each array in an individual well. This array of arrays allows analysis of different multiple samples in parallel. International Patent Applications WO 98/29736 and WO 00/79008 are two illustrative examples of this kind of multi-well plate array where biological materials are arranged on the bottom surfaces of wells. The contents of both of these patent applications are incorporated herein by reference.

Performing parallel experiments using arrays printed on the bottoms of micro-titer plates, however, can be cumbersome. For instance, a considerable amount of pipetting into each individual well is required, even for steps common to all wells, such as washing steps. Additionally, sample image detection can be complicated by at least two factors. First, since samples are located deep in a well, access to the samples creates problems with potential image distortion by shadows and edge effects. Second, if detecting from below the plate, the samples could also be subject to distortions caused by any irregularity of the bottom surface of each well.

A more efficient array platform, thus, would be very attractive to pharmaceutical, biological, or clinical users to perform research in high volume assays or diagnostics.

SUMMARY OF THE INVENTION

The present invention, in one aspect, combines the high volume, mass-processing capabilities of a DNA microarray with the advantages associated with micro-titer plate technology in an "array of arrays." The invention comprises, in part, a device having a support structure with a planar surface, and a plurality of three-dimensional platforms, referred to herein as either "microcolumns" or "micropillars," which project away from the planar surface. A microcolumn has a first or top surface remote from the support structure and at least a second or side surface. A microcolumn has preferably a solid or monolithic structure, which makes the entire design easier to manufacture by various means, and has a shaft of varying height that extends from the support structure. The microcolumn can be made from a multitude of materials, such as any glass, quartz, fused silica, silicon, metal, polymers, plastics, ceramics, or composite materials.

According to one of many possible embodiments, the first surface is substantially planar and has a relatively large surface area for depositing an organized array of biosites. In other words, an array of multiple, different samples of biological material of interest, such as oligonucleotides, DNA, RNA, peptides, proteins, lipid membranes, or other nucleic or cellular matter can be printed or otherwise immobilized on top of each microcolumn. Depending on the actual size of the first surface, an array of varying numbers of biosites could be prepared and attached to each microcolumn. Each microcolumn functions as a microarray of biological samples. Each microcolumn has physical dimensions that will allow it to fit within a well of a corresponding micro-titer plate. This present format permits simultaneous, parallel analysis of a large variety of biological samples under a multitude of experimental conditions while using a single assay device. Accordingly, each well in a corresponding micro-titer plate may contain an experimental condition or reagent that is either the same or a different from another well. In an embodiment, a hollow conduit may extend through the shaft of the microcolumn to permit introduction of reagents or samples directly to the array of immobilized biosites.

According to another embodiment, the first surface of each microcolumn may be left bare. When an array of biological probes is on the bottom surface of each microplate well for a binding assay, a set of microcolumns may be used as cover slips in each well to create a miniature reaction chamber that effectively reduces evaporation and increases binding efficiencies, such as for DNA hybridization, in low volume reactions. A configuration such as described can greatly improve the function of more conventional microplate-based arrays. A permutation of this embodiment, in which arrays are located on both the top surface of the microcolumn and the bottom surface of the well, may increase overall high-throughput capacity, as well as allow one array to be a control for the other. This design also may allow one to sample different species in the same reaction together. That is, one may immobilize one kind of biological or chemical molecule to one surface and another kind to the other surface (e.g., positioning an antibody or protein array on one surface and oligonucleotide or DNA array on the other).

Another aspect of the present invention encompasses a method of performing biological or chemical assays. An array of microcolumns may be used with a micro-titer plate of virtually any geometry, size, or matrix configuration (e.g., 6, 8, 96, 192, 384, 576, 1536-well, etc.). The method comprises: providing an device having at a number of microcolumns projecting away from a support structure, each of said microcolumns having a first surface remote from said support structure and at least one second surface; providing a micro-titer plate with a number of wells corresponding to said number of microcolumns; immobilizing an array of multiple different samples of biological material on either: 1) the first surface of each microcolumn; 2) on an interior (e.g., bottom) surface of each of said wells; or 3) both; inverting said device, whereby the first surface of each microcolumn is oriented toward the bottom surface of each well; inserting said microcolumns into said wells; and introducing an assay reagent solution to perform the assay. The method may further comprise: creating a capillary space between the first surface of each microcolumn and the interior surface of each well; and agitating said device to react said biological material in an assay solution. The method may further include introducing the assay solution through a fluid conduit extending through the microcolumn. The method may further comprise: removing the microcolumn from the well; washing the microcolumns in a second micro-titer plate; drying the first surface and imaging the first surface; and studying or quantifying biological analytes bound to the array on the first surface of said microcolumns.

The wells may contain assay solutions for a variety of uses, such as nucleic acid hybridization, enzymatic assays, lipid, chemical molecule, or cell-based (e.g., transfection or reverse transfection of cells) assays or immuno-assays. In embodiments involving the reverse transfection of cells, an array of different kinds of expressed DNA sequences can be printed on each microcolumn, then cells are laid down on the array over the DNA. (See for comparison and illustration, U.S. patent application Ser. No. 09/962,054, by B. I. Feuer et al., and International Patent Application No. WO 01/20015, by D. M. Sabatini et al., both of which are incorporated herein by reference.)

An advantage of the present invention is the possibility for physical agitation of a reaction solution to promote biological reactions. Since an array of microcolumns is physically a separate element from its corresponding microtiter plate, it becomes possible to "stir" (i.e., move physically up and down, side to side, or swirl around) the solution within each well. This stirring action increases the microfluidic interactions of the immobilized biological probes and their targets. Conventional micro-titer plate techniques cannot perform this kind of physical agitation. Moreover, the present invention can operate at small volumes of reagents and samples most current micro-titer plate assays do. This provides savings in costs and conservation of scarce samples, since less reactants is needed to conduct an assay.

Further, according to another embodiment, micropins may be project away from the first surface of a microcolumn. A sample of biological material could be attached to the top surface of each micropin. Since each micropin has a minimal top surface area and does not have a peripheral region that may attract non-specific binding of target molecules, they offer the possibility of reducing background signal when imaging samples. Micropins raise the sample biosites above and away from surrounding regions, which recede into the background when imaged. Imaging techniques such as two-photon fluorescence imaging, microscopy, or spectroscopy may be employed.

The present invention, in an embodiment, also relates to the use of microcolumns for screening of chemical molecules or drug compounds in biochemical or cell assay formats. Chemical probe arrays either on the first surface of each microcolumn or on the bottom of microplate wells may be used in direct labeled or non-labeled binding assays with different types of targets (e.g., purified proteins, membranes, carbohydrates, or nucleic acids) or cellular material. Further, microcolumn-based devices may be used with photo-induced release of chemical molecules, such as drug compounds, from arrays on their first surfaces. One may use photomasks to selectively release and identify active compounds in a target pool.

Additional features and advantages of the invention will be set forth in the detailed description that follows. It is to be understood that both the foregoing general discussion and the following detailed description and examples provided herein are merely exemplary of the invention, and are intended to provide an overview or framework for understanding the nature and character of the invention as it is claimed.

BRIEF DESCRIPTION OF THE DRAWINGS

FIG. 10A depicts a view of the bottom wall of a well in a micro-titer plate, wherein the bottom wall has been treated to have both a hydrophobic and hydrophilic region.

FIG. 10B depicts a liquid reagent contained within the hydrophilic region at the center of the well bottom, and precluded from the hydrophobic region along the periphery.

FIG. 10C depicts a three-dimensional perspective view of the situation in FIG. 10B.

DETAILED DESCRIPTION OF THE INVENTION

Definitions

Figure 1A:
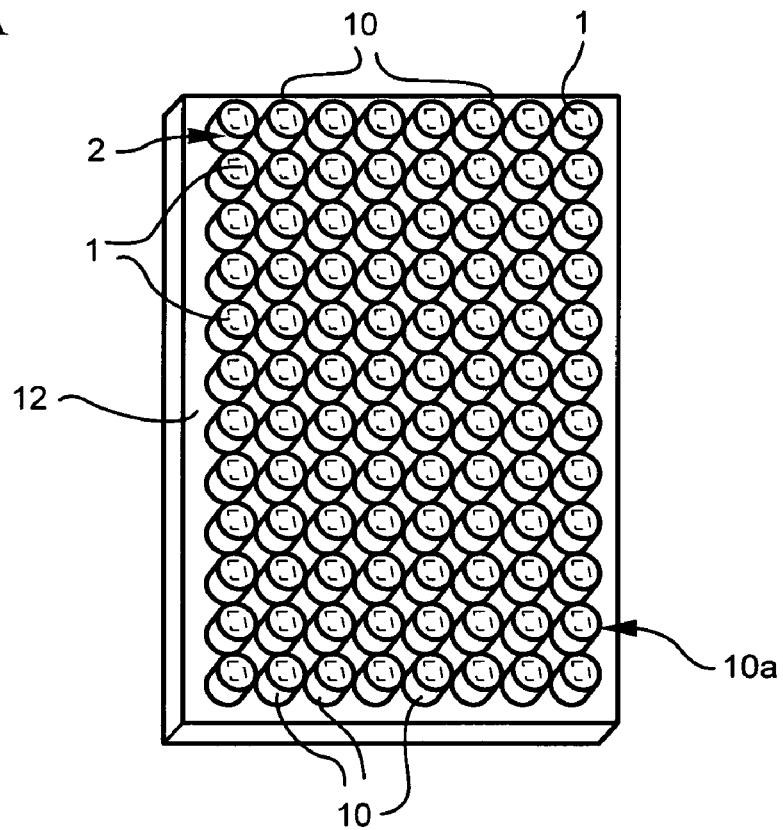
FIG. 1A depicts as a schematic of a perspective view from above of a planar support with a set of 96 three-dimensional column-shaped platforms, according to an embodiment of the present invention.

The term "biological material" or "biological analyte" as used in this application refers to a variety of biological molecules or substances. These molecules may include, but are not limited to: nucleic acid sequences (e.g., DNA, RNA, oligonucleotides, cDNA, plasmids, etc.), peptides, proteins, lipids, protein or lipid membranes, organic or inorganic chemical molecules (e.g., pharmaceutical drugs or other compounds), virus particles, eukaryotic or prokaryotic cells, sub-cellular components or organelles, and other matters. Preferably, the term "biological material" is used to refer to biological molecules or substances immobilized on a surface, while, the term "biological analyte" refers to biological molecules or substances that are subsequently attached to the biological material after performing a binding assay.

The term "biosite" as used herein refers to a discrete area, spot or site on the active surface of an array, or base material, comprising at least one kind of immobilized biological material for use as a probe or other functionality.

The term "microcolumn," "micropillar platform," or "platform" as used in herein refers to any three-dimensional raised surface of varying vertical dimension (height) and design upon which biological materials can be deposited. As seen in the group of FIGS. 1 and 2, the biological materials 1 are preferably arranged in an array 2 on the first surface 3 of each microcolumn 10, which is remotely located from a support structure 12. Each microcolumn need not necessarily be in the form of a single, unitary pillar having a constant cross-sectional dimension along its height. Other designs with varying cross-sectional dimensions along the vertical dimension 4 are included within the scope of the invention, so long as the other designs embody a substantially flat or planar first surface 3 elevated out of the general plane of a support structure 12. Preferably, each microcolumn is orthogonal to the support structure.

The term "micro-titer plate," "microplate," or "multi-well plate" as used in this application refers to a well or reservoir plate of various designs as used in biological or chemical analysis. The term "well" or "micro-titer well" relates to the wells 6 themselves. Although the actual number of wells is not limiting to the invention, a micro-titer plate includes any plate having at least one reservoir or well for the containment of a liquid medium. Such a micro-titer plate can range from having one large reservoir to more than 1,536 individual wells, but preferred embodiments contain 6, 8, 12, 24, 48, 96, 384, 480, 576, or 1536 wells, etc. Other intermediate configurations are also included.

The term "micropin" as used herein refers to a very fine, rod or pin-like structure that extends vertically from the first surface of a microcolumn. Each micropin 16 has a first surface 16a and at least a second surface 16b. The micropin could possibly be formed in a number of ways out of a variety of materials. Materials such as any glass, quartz, fused silica, silicon, metal, polymer, plastic, ceramic, or composite material having the shape of a rod, pin or fiber could be employed depending on their actual use. Preferably, a micropin is cylindrical and has a circular cross section of constant radius, R. In no way, however, are other embodiments with different cross-sectional shapes (e.g., oval, square, triangular, polygonal, etc.) excluded from the context of the present invention.

The term "planar support" or "support structure" as used herein may comprise any rigid, substantially flat substrate or plate from which three-dimensional platforms project away. A support structure may, for example, form the lid of a micro-titer plate. The support structure can also include a slide or pane of glass, ceramic, polymer, or plastic, or strips or sheets of metal.

Description

The present invention in one aspect embodies an apparatus for biological and chemical analysis. The present invention brings together microarray technology with multi-well plate technology to provide in a single apparatus a simple, yet highly effective means for achieving high throughput analysis of genetic or other biological moieties in small, thematic arrays in a multiplexed format. The advantages associated with parallel analysis have motivated researchers to develop various devices and methods in the quest for high throughput capability. For instance, Monk et al. in U.S. Pat. No. 6,022,700, incorporated herein by reference, describe a biological sample preparation device and a method for its use to prepare and visualize cultured cells in high resolution, single or multi-label, 2 dimensional, or 3-dimensional fluorescent microscopy. Biological samples, like cells, attached to a surface of a support member can be studied under the lens of a microscope. Monk's design is used for visualizing biological samples attached to the support member; however, it is not meant for studying and quantifying biological samples in assay solution. Modlin et al. described in U.S. Patent Publication No. US2001/0006417 A1, incorporated herein by reference, another example of devices and methods for containing and analyzing small sample volumes that are sandwiched between solid surfaces. Modlin's apparatus acts as part of an optical device that displaces fluid to reduce or modulate the amount of unbound luminophores in the optical pathway when read through the device. Unbound luminophores can interfere with optical analysis since they increase background signal.

According to the present invention, the basic design of an array device comprises at least one member, preferably a plurality, elevated from the plane of a support structure. Conceptually, the present invention can be seen as microtiter wells that have been turned "inside-out" to enable greater ease in performing each assay and fabrication of the device. Each member, also known as a microcolumn 10, has a substantially planar or flat first surface 3 remote from the support structure and at least one second surface 5. The microcolumn is preferably a monolithic structure. The flat first surface of each microcolumn has a relatively large and preferably uniformly smooth area.

A microcolumn offers an exposed first surface, which is more accessible than the bottom of a micro-titer well for printing or depositing samples of multiple biological probes. A plurality of biosites 1a can be deposited, for instance, by various printing methods on the first surface of each microcolumn in a rectilinear array (e.g., in configurations of 8×12, 10×10, 12×12, 16×24, 25×25, 32×48, 50×50, 75×75, 100× 100, more or less). The actual numbers or arrangement of biosites is not necessarily a limiting factor. An advantage of a rectilinear arrangement of biosites is that the microcolumn has a known registration of biological materials, especially for genomic or nucleic applications. This is a convenient feature for researchers, who need not resort to complicate labeling schemes. Hence each microcolumn hosts an array of multiple, different biological materials in the format of a microarray.

Moreover, a microcolumn's exposed first surface affords easier access for studying biological moieties that bind in solution with the array of probes. For example, the surface may be closely approached either with an imaging device to examine the assay. The present invention is not part of an optical device, but rather furnishes, in part, a support for immobilizing an array of biological probes that can be imaged without the need to reduce background signal in solution. Following the assay, the microcolumn is withdrawn from the well and dried prior to imaging biological analytes of interest bound to the array.

The present microcolumn apparatus is designed to work in conjunction with microtiter-well plates of preferably, standard matrix configurations and physical dimensions. Hence, each microcolumn preferably has physical dimensions—diameter (cross-sectional width) and height—that fit within a corresponding-sized well or reservoir (e.g., a well in a standard 96-well matrix with a diameter of about 5 mm, a well in a 384-well matrix with a diameter of about 3 mm, or a well in a 1536-well design with a diameter of about 0.5 mm, or any size in between). The actual size of each corresponding well may vary and is not necessarily a limiting factor to the microcolumn. A microcolumn may have a cross-sectional dimension that ranges in size from about 0.1 mm to about 10 cm.

Figure 3A:
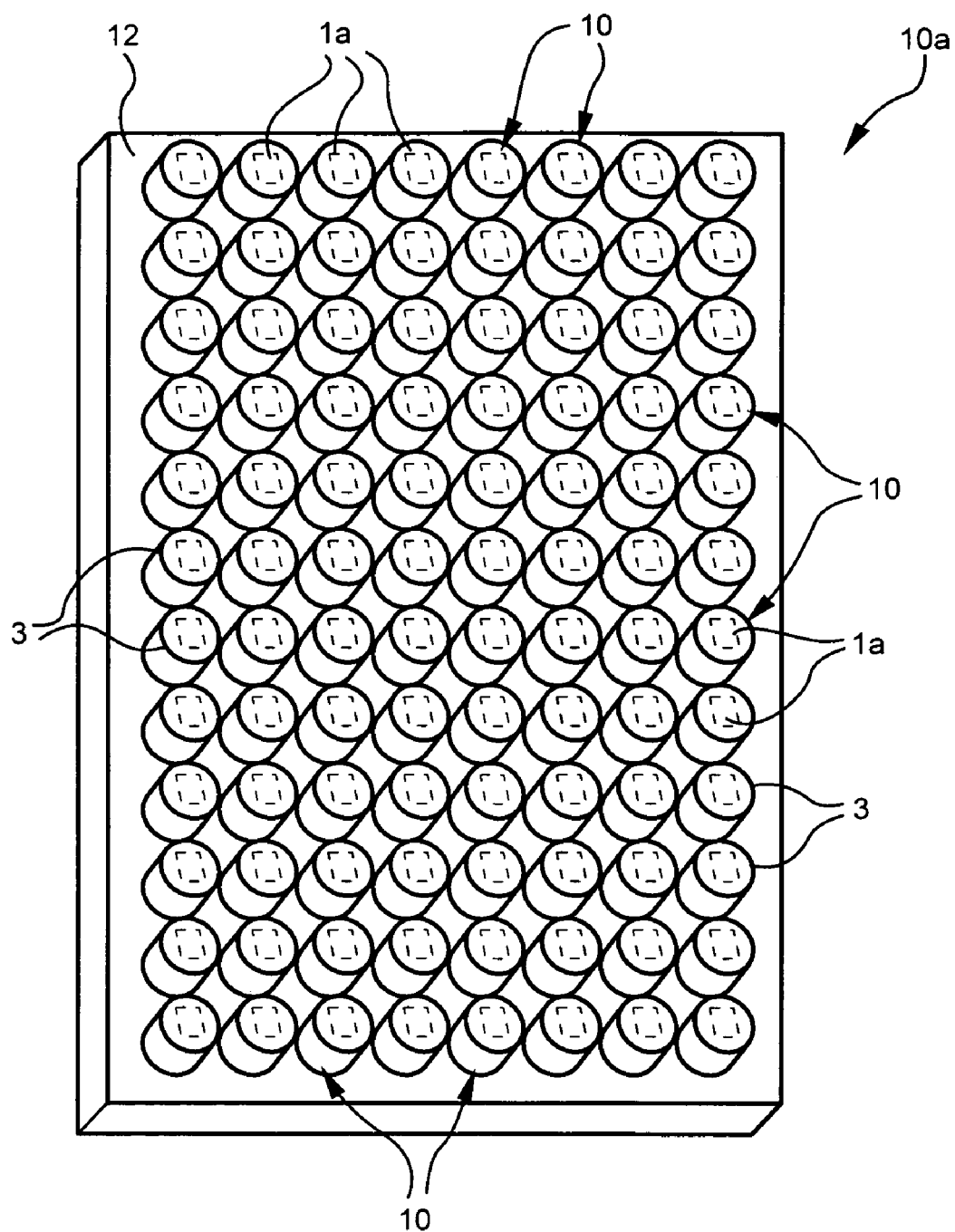
FIG. 3 depicts a platform with a 96-microcolumn array (FIG. 3A) and a 96-well micro-titer plate (FIG. 3B) side by side, and shows that microcolumns correspond to micro-titer wells.
Figure 3B:
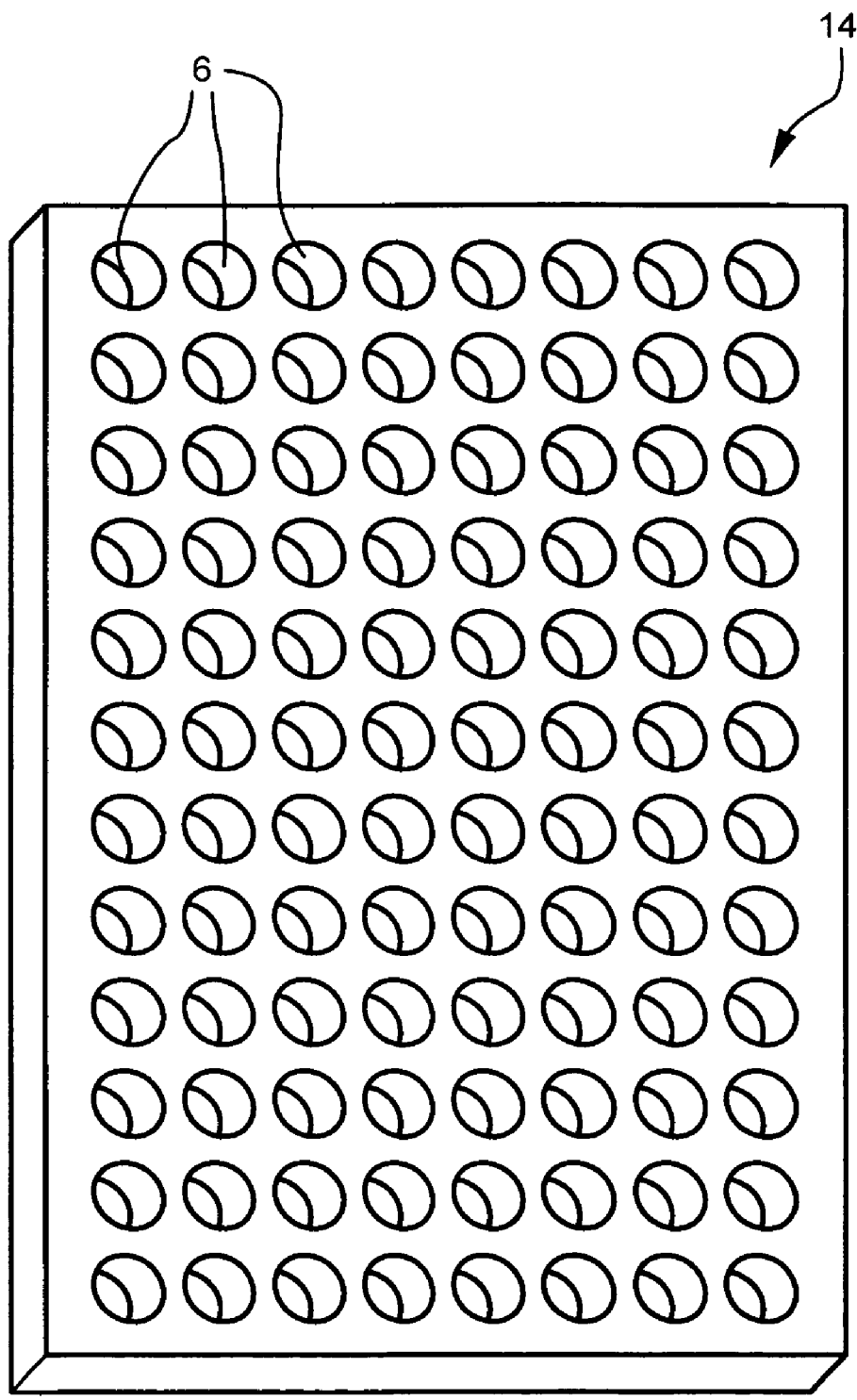

FIGS. 1A, 1B, 1C, 1D, and 1E are schematic representations of microcolumns 10 according to different embodiments of the present invention. Multiple arrays of biological materials, like oligonucleotide or DNA probes, can be immobilized on the first surfaces of microcolumns. FIG. 1A shows a perspective view from above of a planar support 12 having a set of microcolumns 10 arranged in a rectilinear matrix of 96 columns 10a, for use in conjunction with a standard 96-well microtiter plate 14 like that shown in FIG. 3B. The support structure or plate with the array of three-dimensional microcolumns, according to the embodiment of FIG. 1A, would have length and width dimensions equal to a standard micro-titer plate with a 96-well format, of approximately 5.0±0.2 inches long, by about 3.3±0.2 inches wide. Seen side by side in FIG. 3, the microcolumn matrix 10a of FIG. 3A corresponds and fits within the wells 6 of the micro-titer plate 14 of FIG. 3B.

Figure 1B:
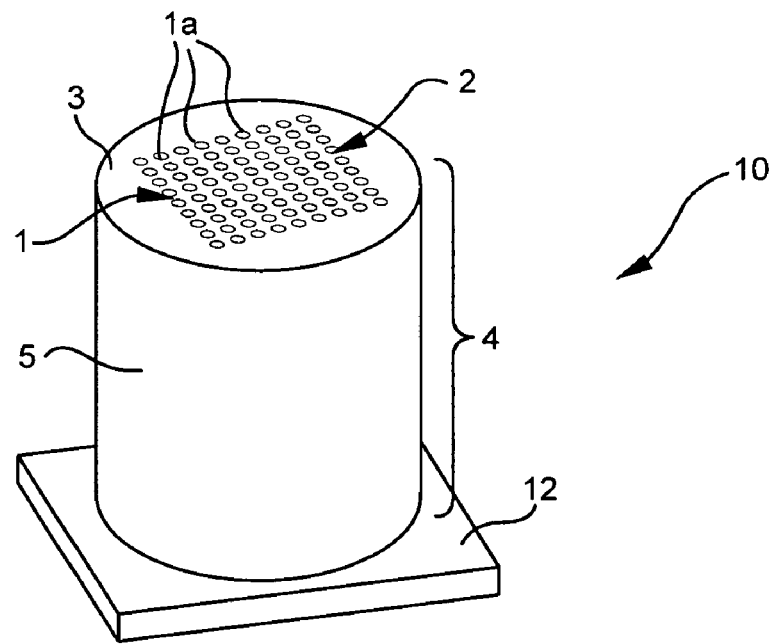
FIG. 1B depicts an enlarged view of one column-shaped platform of FIG. 1A, having an array of biological materials disposed on its first or top surface, according to an embodiment of the present invention.
Figure 1C:
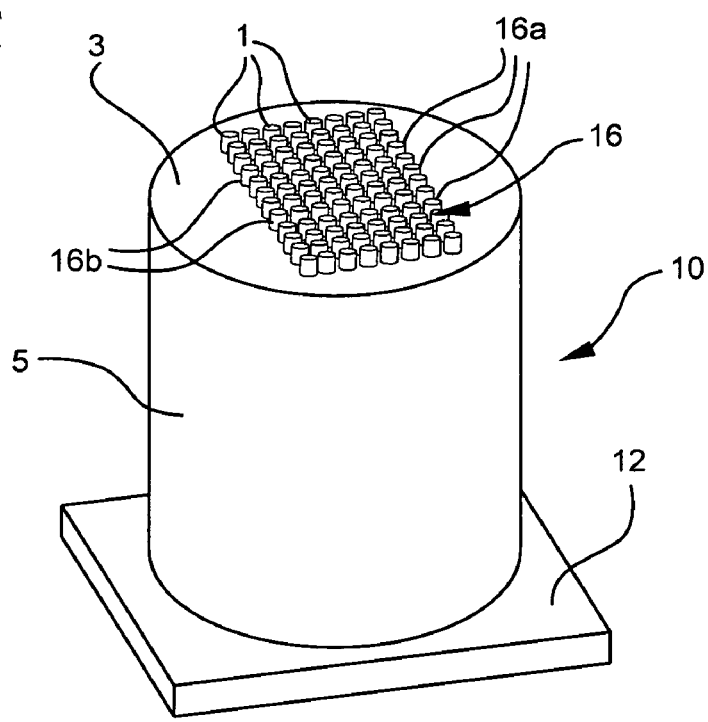
FIG. 1C depicts an enlarged view of one column-shaped platform having disposed on its first surface a set of micropins, according to an embodiment of the present invention.

FIG. 1B shows an enlarged view of one typical microcolumn 10 platform on a planar support structure 12. An array of biological materials 2 is deposited on the first surface 3 of the microcolumn 10. In an alternate embodiment, FIG. 1C shows an enlarged view of a platform comprising a number of micropins 16, or rod-like projections, located on the microcolumn's 10 first surface 3.

Micropins 16 extend away from the plane of the first surface 3 of the microcolumn 10, and are preferably oriented orthogonally to the plane of the first surface of the microcolumn. Samples of biological material 1 are attached to the first surface of each micropin 16. The first surface 16a of each micropin preferably is substantially planar or flat, but can also be rounded, hemispherical, or even conical with a point. Micropins 16 collect or hold liquid samples of biological material 1 by at least two possible methods. In one way the micropin can have a first hydrophilic wetting surface and at least a second 16b hydrophobic non-wetting surface. The wetting surface permits biological material to attach and be contained by the non-wetting surface. In a second, alternate way, a roughened top surface that wets by fluid entrapment can be employed. That is, fluid is entrapped due to multiple fluid contact angles. Although the actual number of micropins 16 located on top of a microcolumn 10 is not a limiting factor, preferably groupings of micropins 16 can range from about less than ten or twenty to an array of about 100 or more.

Figure 1D:
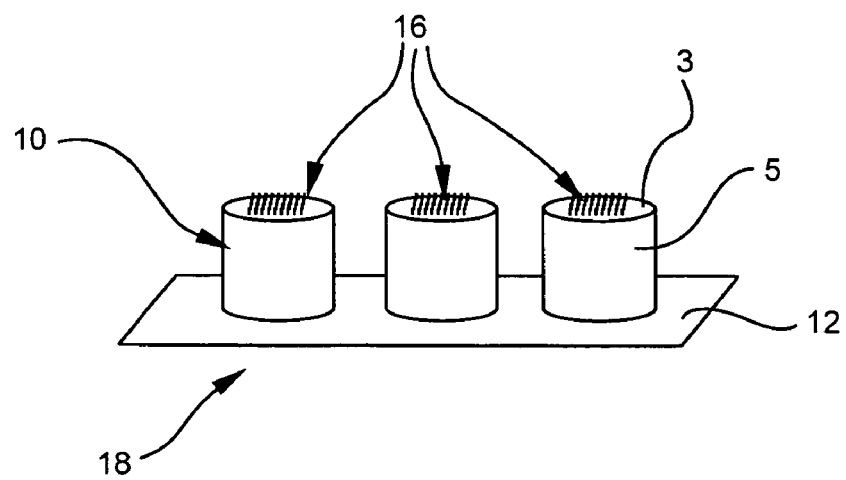
FIG. 1D shows a three-microcolumn strip, according to the present invention.
Figure 1E:
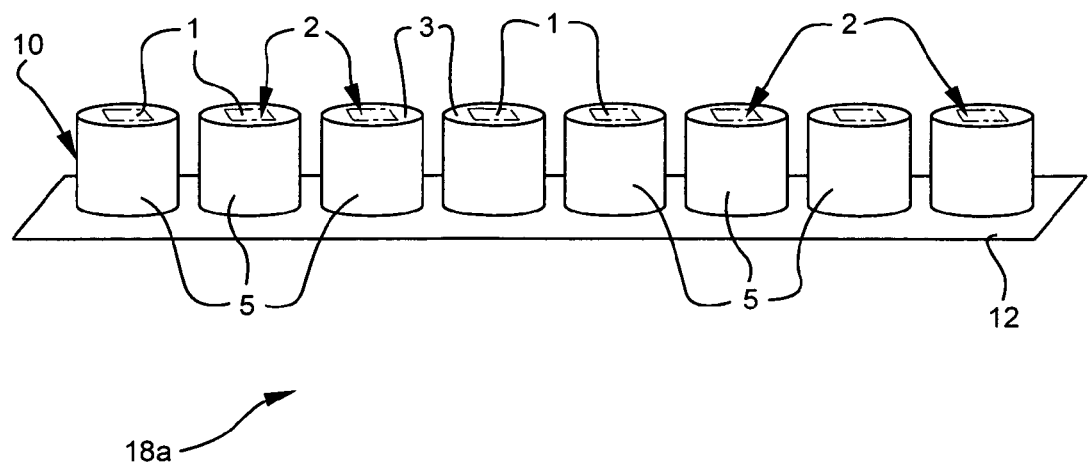
FIG. 1E shows an eight-microcolumn strip, according to the present invention.

FIGS. 1D and 1E present other embodiments that may be used in test kits. FIG. 1D shows a three-microcolumn strip 18, and FIG. 1E shows an eight-microcolumn strip 18a, which can be employed, respectively, with a corresponding three-well and eight-well strip plate. Other possible variations in microcolumn strip designs, such as 6, 12, 16, 24, 32, or 48-microcolumns, etc. are also comprehended.

Figure 2A:
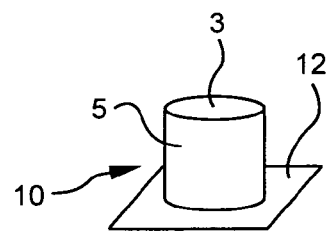
FIGS. 2A, 2B, 2C 2D and 2E represent alternate embodiments for a micro column.
Figure 2B:
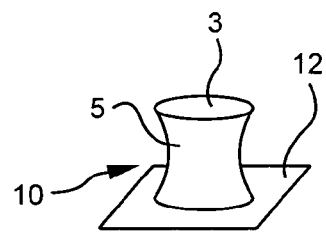
Figure 2C:
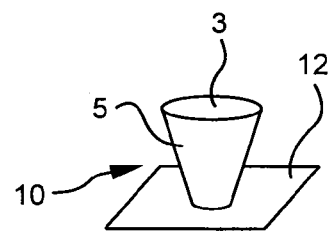
Figure 2D:
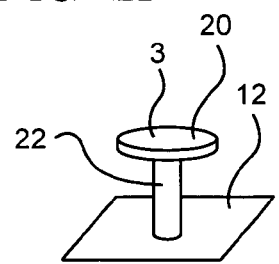
Figure 2E:
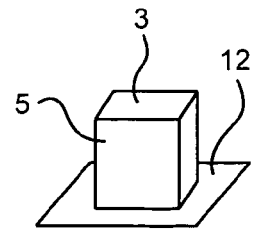

FIGS. 2A, 2B, 2C, 2D and 2E represent alternate microcolumn designs. The apparatus of FIG. 2A is a typical cylinder configuration. FIG. 2B shows a microcolumn in the shape of an hourglass. The cross-sectional dimension changes—narrowing and widening—as one progresses from top to bottom of the pedestal. FIG. 2C shows an inverted frusto-conical pedestal, while FIG. 2D illustrates a microcolumn with a so-called "plate and stem" design, which may be likened to a "flat-head nail," wherein the plate section 20 forms the first surface 3 and the stem 22 forms the pedestal of the microcolumn 10. FIG. 2E shows a square configuration for square micro-titer wells. The particular designs of FIG. 2B, 2C, 2D, and their variations can prevent cross-talk between samples in a micro-titer plate. Without sacrificing the total surface area of the microcolumn first surface 3, an increase in the space or distance between the microcolumn and a sidewall of a micro-titer well will avoid potential contamination problems associated with capillary action. When the microcolumn is inserted into a micro-titer well, reaction fluids will be less able to wick-up in the spaced between the sidewalls of the well and the microcolumn.

Figure 4:
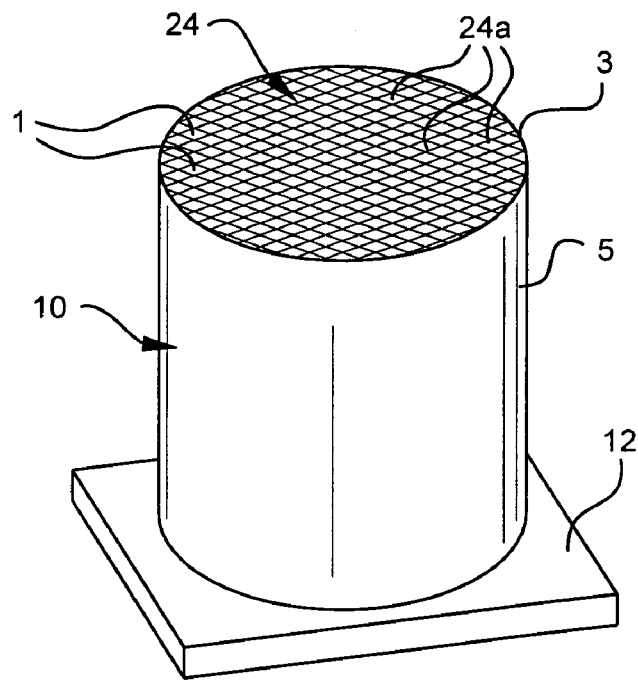
FIG. 4 shows a schematic view of a microcolumn with a "sliced array" of biological materials deposited on its first surface, according to an embodiment of the present invention.

An alternative embodiment as shown in FIG. 4, comprises a microcolumn 10 having attached to its first surface 3 a "sliced array" 24, which is described in detail in International Application Nos. WO9955460 and WO9955461, both by Borrelli et al., the contents of which are incorporated herein by reference. This embodiment can greatly simplify the deposition or printing of biological materials 1. According to the sliced array technique, a very thing slice is cut off of a reduced size portion of a redrawn capillary imaging reservoir. Each slice is preferably approximately between about 4 nm and about 10 nm in thickness, although any sliced thickness may be possible. The slices take the form of a sheet comprising a lattice-like network 24a formed by the channel walls of the redrawn capillary imaging reservoir and defining a plurality of containment spaces, each having sidewalls and an open top and bottom, for biological samples and a different known binding entity.

Figure 5A:
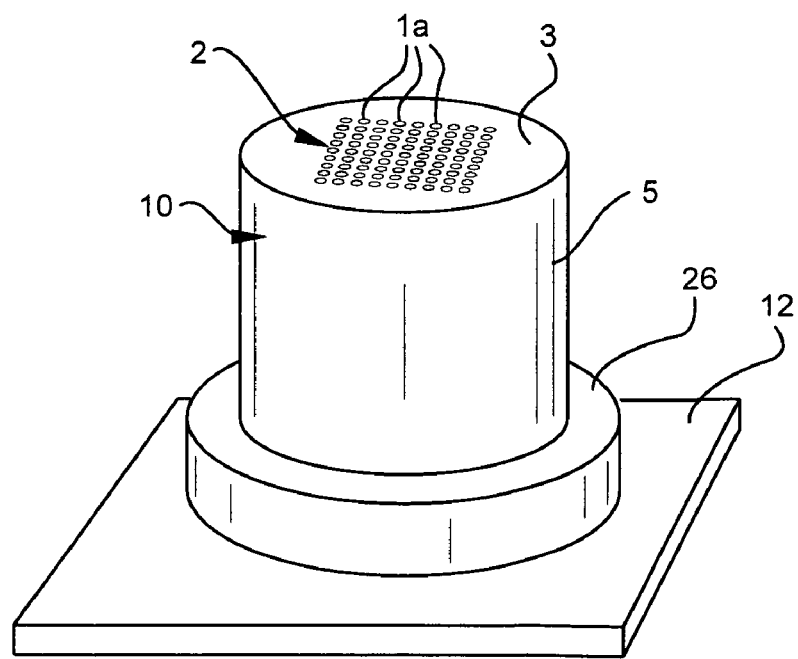
FIG. 5A shows an enlarged view of an embodiment with a seal located at the base of a microcolumn for sealing the opening of a corresponding micro-titer well.
Figure 5B:
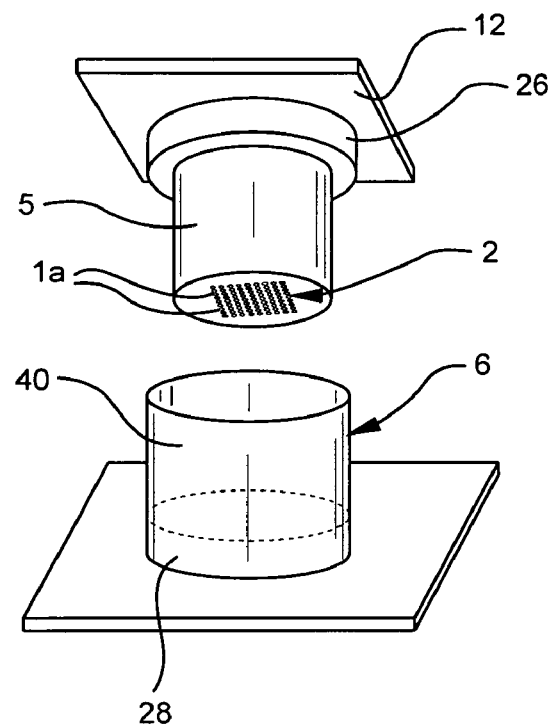
FIG. 5B shows the interaction of the embodiment showing in FIG. 5A with a micro-titer well.
Figure 5C:
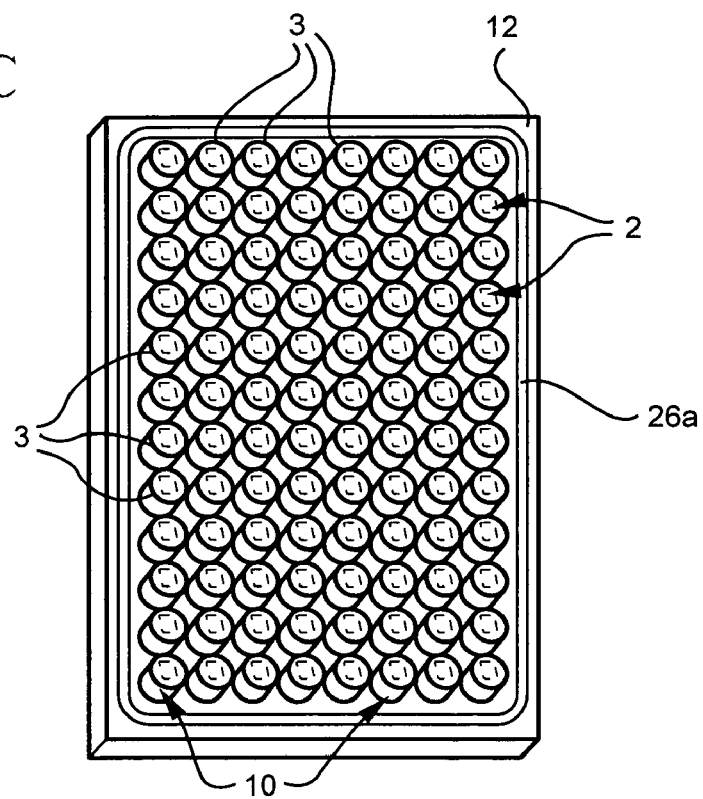
FIG. 5C shows a plate having an array of 96 microcolumns with a seal around the outer perimeter of the plate.

According to some designs, a pre-formed seal may be incorporated around either the base of the microcolumn or the opening of its corresponding micro-titer well, or both, or around the periphery of an entire multi-well plate. FIG. 5A illustrates a microcolumn 10 with an elastomer or rubberized annulus 26 encircling its base. The annulus 26 is designed to conform to the upper rim of a micro-titer well 6 and seal the micro-titer well 6 when the microcolumn 10 is introduced into the micro-titer well, like that shown in FIG. 5B. The seal 26a could also, for instance, be located long the outer or peripheral edge of the planar support structure 12, which holds the microcolumns 10, for example as on the lid of a micro-titer plate, as shown in FIG. 5C. Both kinds of sealing features could eliminate sample cross-contamination during assay development, or minimize assay variability by controlling evaporation of liquid reagents or the micro-environs of the samples in the plate. Moreover, individual temperature control devices could be built into each microcolumn to permit greater temperature flexibility in assay development.

Figure 6A:
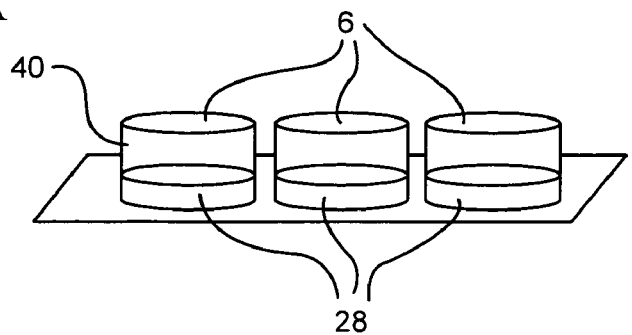
FIGS. 6A and 6D show a partial schematic view of a number of wells from the micro-titer plate of FIG. 3B.
Figure 6B:
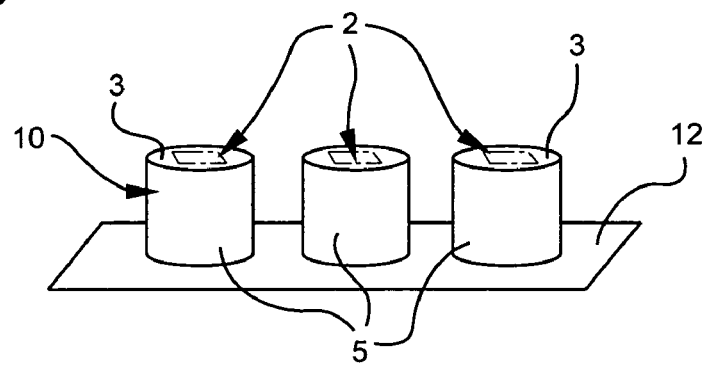
FIG. 6B shows a partial schematic view of a number of microcolumns according to the embodiment of FIG. 1B.
Figure 6C:
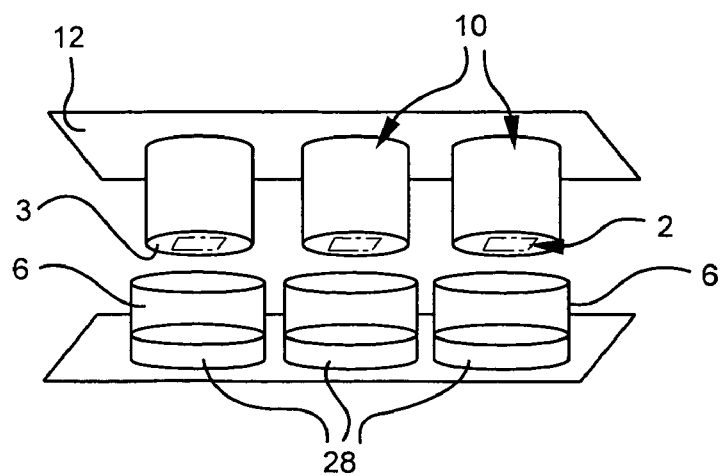
FIGS. 6C and 6F, respectively, demonstrate the way that microcolumns of FIGS. 6A and 6D and micro-titer wells of FIGS. 6B and 6E function together according to an embodiment of the present method for carrying out an assay.
Figure 6D:
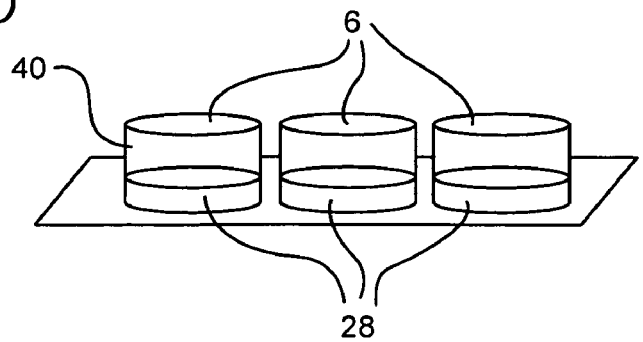
Figure 6E:
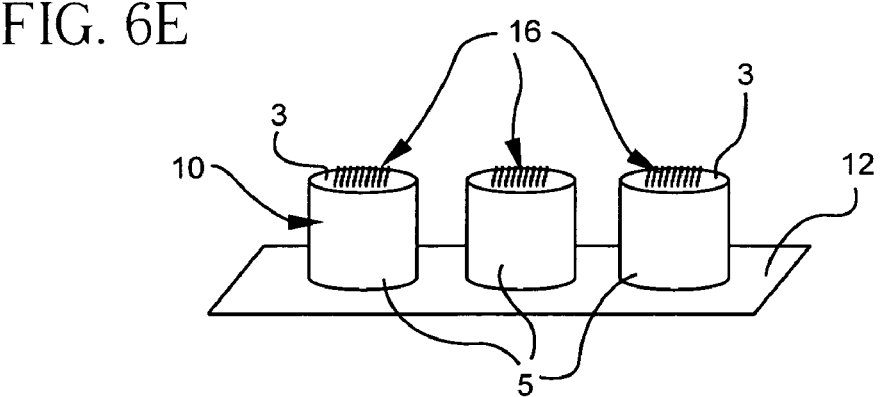
FIG. 6E shows a schematic view of a number of microcolumns with micropins according to the embodiment of FIG. 1C.
Figure 6F:
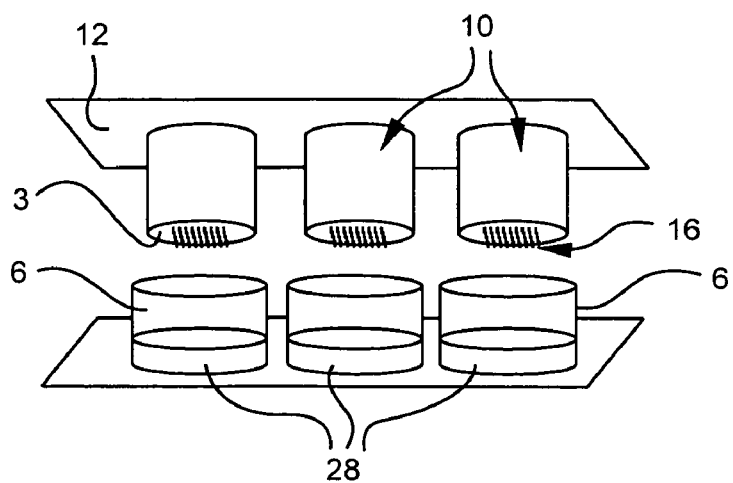

The present invention also encompasses a method for performing an assay. The depictions in FIGS. 6A, 6B, and 6C demonstrate how microcolumns could be used according to an embodiment of the present method. FIG. 6A represents a number of corresponding micro-titer wells 6 from the micro-titer plate of FIG. 3B. FIG. 6B shows an enlarged schematic view of a number of microcolumn 10 platforms of the kind shown in FIG. 1B. FIG. 6C illustrates the interaction between microcolumns 10 and micro-titer wells 6. (Alternatively, FIGS. 6D, 6E, and 6F, respectively, represent micro-titer wells 6, microcolumn 10 platforms with micropins 16 of the kind shown in FIG. 1C, and their interaction.) The method comprises a number of steps. First, a device with has at least one microcolumn is provided. An array of multiple different samples of biological material is immobilized on either: 1) the first surface of each microcolumn; 2) on a bottom surface of each of said wells; or 3) both. In particular, many different biological materials 1 are set down together in an array on the first surface 3 of each microcolumn 10. When ready to perform the assay, the microcolumns are inverted, whereby the first surface of each microcolumn is oriented toward the bottom surface of each well, and inserted into or otherwise engaged with a corresponding well 6 or reservoir in a microtiter plate. A variety of reagent solutions could be used. Depending on the desired application, the reagents can be for DNA hybridization, protein and antibody assays, or cell transfection and reverse cell transfection assays. Each microcolumn 10 is designed to specifications such that its first surface—or the first surfaces of micropins 16—does not make direct contact with the bottom wall 30 of a micro-titer well 6 or reservoir, but rather comes only into close proximity with the bottom wall 30. The entire apparatus can be physically agitated, either by hand or machine, to promote reaction of the biological materials 1 with the liquid reagent 28. After the reaction completes, the apparatus is withdrawn and its first surface imaged to study the biological or chemical reaction.

Figure 7:
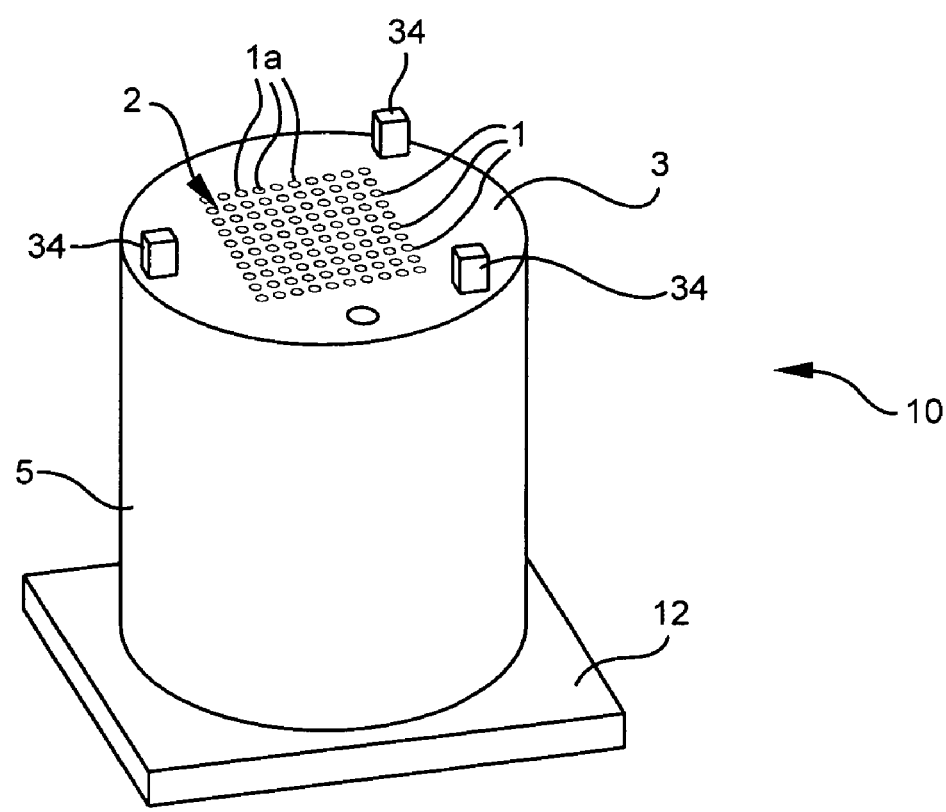
FIG. 7 depicts an embodiment of a spacer located along an edge of the first surface of the microcolumn.

The present invention when used with a microplate provides an assay chamber for efficient low volume binding reactions. Various means can be used to maintain a constant capillary space 32 between the inverted first surface of a microcolumn 10 and the opposing bottom wall 30 of a micro-titer well 6. For instance, a set of at least three spacers 34, like that shown in FIG. 7, may be employed. The spacers 34 project either from an edge of the first surface 3 in a substantially orthogonal orientation to the plane of the first surface, or (not shown) from a second or side surface 5. In an alternate arrangement and embodiment, the three spacers also can take the form of hemispherical beads, which are equidistantly located on the first surface near the edge of the first surface, where the first surface meets the second surface of the microcolumn. Also envisioned is a slightly protruding, continuous ridge or bead that runs along the edge of the first surface.

Figure 8A:
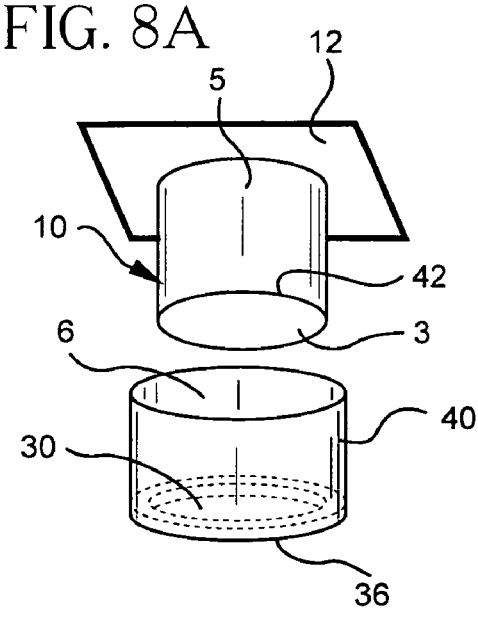
FIG. 8A depicts a raised rib type spacer located around the periphery of the bottom of a micro-titer well, for maintaining a constant distance for a capillary space between the bottom and the first surface of a microcolumn.
Figure 8B:
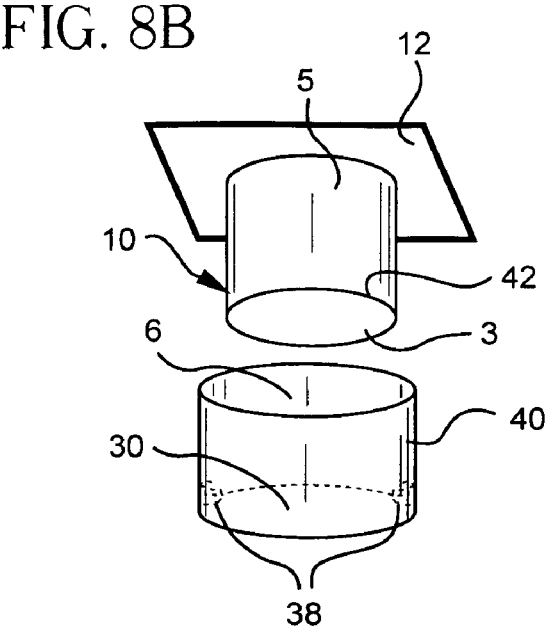
FIGS. 8B and 8C depict two embodiments of flange type spacers for maintaining a constant distance for a capillary space between the bottom and the first surface of a microcolumn.
Figure 8C:
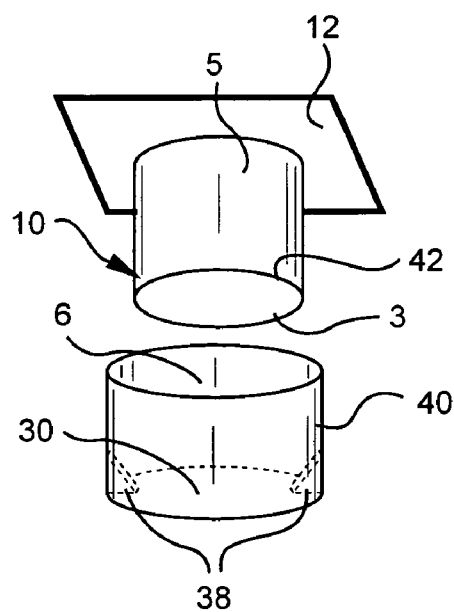
Figure 8D:
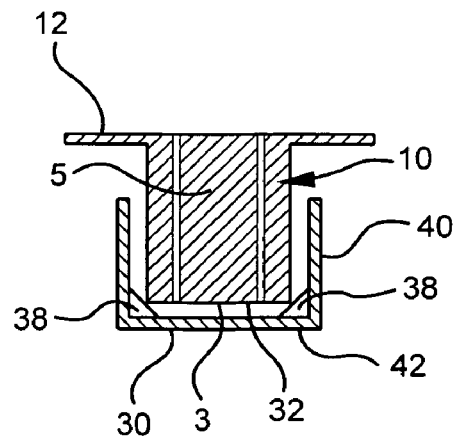
FIG. 8D depicts the first surface of a microcolumn resting on a flange for maintaining a capillary space between the first surface and the bottom of a micro-titer well.

Other kinds of spacers, alternatively, may be used to maintain a constant distance in the capillary space 30 between the two opposing surfaces 3, 32. These spacers, like either a raised rib 36 or a flange 38, as illustrated in FIGS. 8A, 8B, and 8C, are located in the micro-titer wells. In FIG. 8A, the rib 36 is disposed on the interior bottom wall 32 along the circumference or periphery of the bottom wall 30 where it meets a sidewall 40 of the micro-titer well 6. Also located at the juncture of the bottom wall and sidewall, as seen in FIGS. 8B and 8C, the flange 38 extends inwardly from the sidewall. The flanges 34 can be shaped as either a step (FIG. 8B), a triangle (FIG. 8C), a quarter circle such as of a bead or dowel (not shown), or any other shape. Without touching any biosites 1*a* that may be immobilized on the first surface 3, the rib 36 or flange 38 provides a resting surface for an edge 42 of the microcolumn's first surface 3. As seen in cross-section in FIG. 8D, the edge 42 is placed against the flange 38, such that the first surface is opposite and spaced apart from the micro-titer well's bottom wall. According to these embodiments, the height of the spacer, rib or flange determines the actual distance (capillary space) of separation between the microcolumn first surface and micro-titer well bottom wall.

Despite the advances of array technology, the ability to detect biological molecules and biological reactions with better sensitivity still remains a critical need for biological, molecular, pharmaceutical, and medical applications. One of the problems inherent to conventional microarrays is the rather poor signal to noise ratio, which becomes an issue for highly sensitive applications. Increased sensitivity of detection is most efficiently addressed by eliminating background noise, as contrasted with increasing signal.

The present invention, especially those embodiments employing micropins, can provide improved sensitivity for the detection of biological molecules and biological reactions. Although not intended to be bound by theory, it is believed that each micropin may be shaped in certain designs to condensed activation light incident from binding the pin at the pin tip, and may be used to perform non-linear detection using two-photon fluorescence imaging, microscopy, or spectroscopy. (See, e.g., Y. Shen et al., *Applied Physics Letters*, 2000, 76 (1), 1-3; X. Wang et al., *J. Biomed. Opt.*, 2001, 6 (3), 319-325.) Physically raising the biological material away from the surrounding regions, which become part of the background when imaged, and moving the focal area of detection to the first of a pin increases the ability to discriminate optically by depth of focus above the plane of the background, hence, workers can image the samples more easily, with greater sensitivity and less background signal. The three-dimensional configuration of a micropin array permits the use of unique optics for high sensitivity detection by spatial discrimination. Increased sensitivity, moreover, conveys added benefits. With a highly sensitive tool would permit workers to detect very small changes in a biological reaction, and they would not need to use as much biological material and reagents to perform an analysis as now. Both of these factors can reduce costs substantially and enable workers to conserve biological samples of limited availability.

In another application, the present microcolumn array design could be used as a tool for mass spectroscopy analysis. Generally in mass spectroscopic analysis, a laser beam ionizes a sample. The current technology, based on microplate designs, is rather constrained since samples are located on the bottom of a well, where they are more difficult to reach with a laser. Biological material immobilized on the microcolumn's exposed first surface is more readily accessible to the laser. Hence, microcolumns make high throughput analysis easier for mass spectroscopy (MALDI/TOF) instruments.

Figure 9:
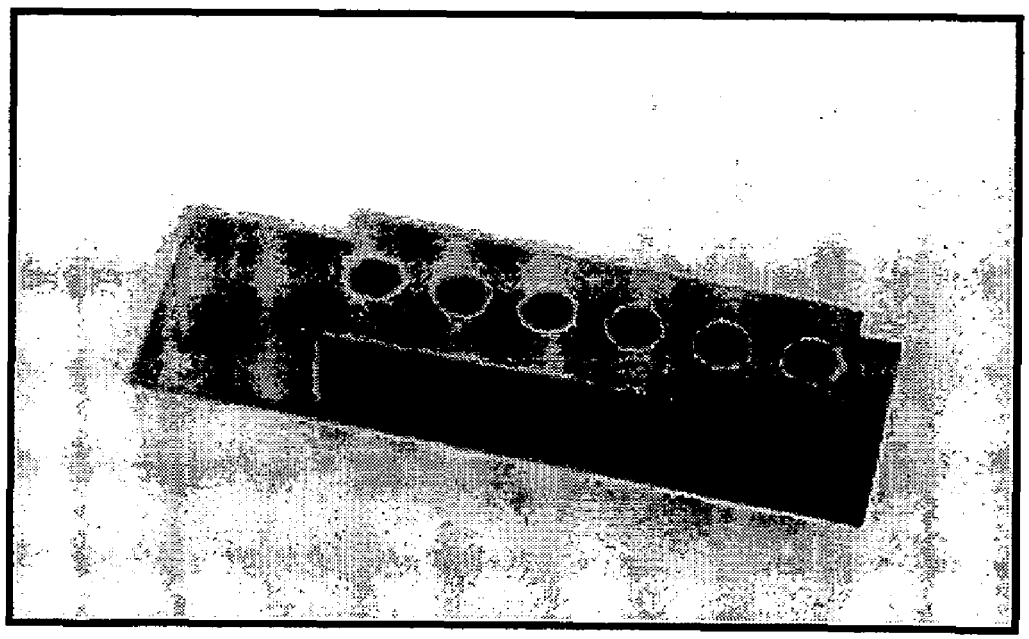
FIG. 9 shows an adaptor, which holds a microcolumn array in place for use with an optical scanning device.

To facilitate the detection of arrays on first of microcolumns using currently available slide scanners, an "adaptor" may be employed to hold the microcolumn array with an optical device. FIG. 9 shows an adaptor for a six-microcolumn strip. The adaptor is made of either black or dark-colored hard rubber or polymer materials and fits around each microcolumn to situate the first surface of the array at the appropriate position for optical scanning. The adaptor may cover the edge of each microcolumn to visually isolate biosites and avoid edge-effect distortions. Depending on the particular design, an adaptor can remove optical interference such as refraction, birefringence or other light scattering during the imaging process. Other adaptor formats are envisioned to make microcolumn arrays more compatible with either current scanning devices or for other viewing methods. For instance, an adaptor can be made to enable one to image simultaneously a full array of microcolumns, which can either be formed as an integral part or post-fabrication-fitted to an array of microcolumns. To make the array conform to standard microplate dimensions of about 5.0±0.2 inches long, by about 3.3±0.2 inches wide, and 0.56±0.02 inches high, an adaptor would favor easier, robotic handling and direct scanning of each microcolumn's first surface.

Figure 14:
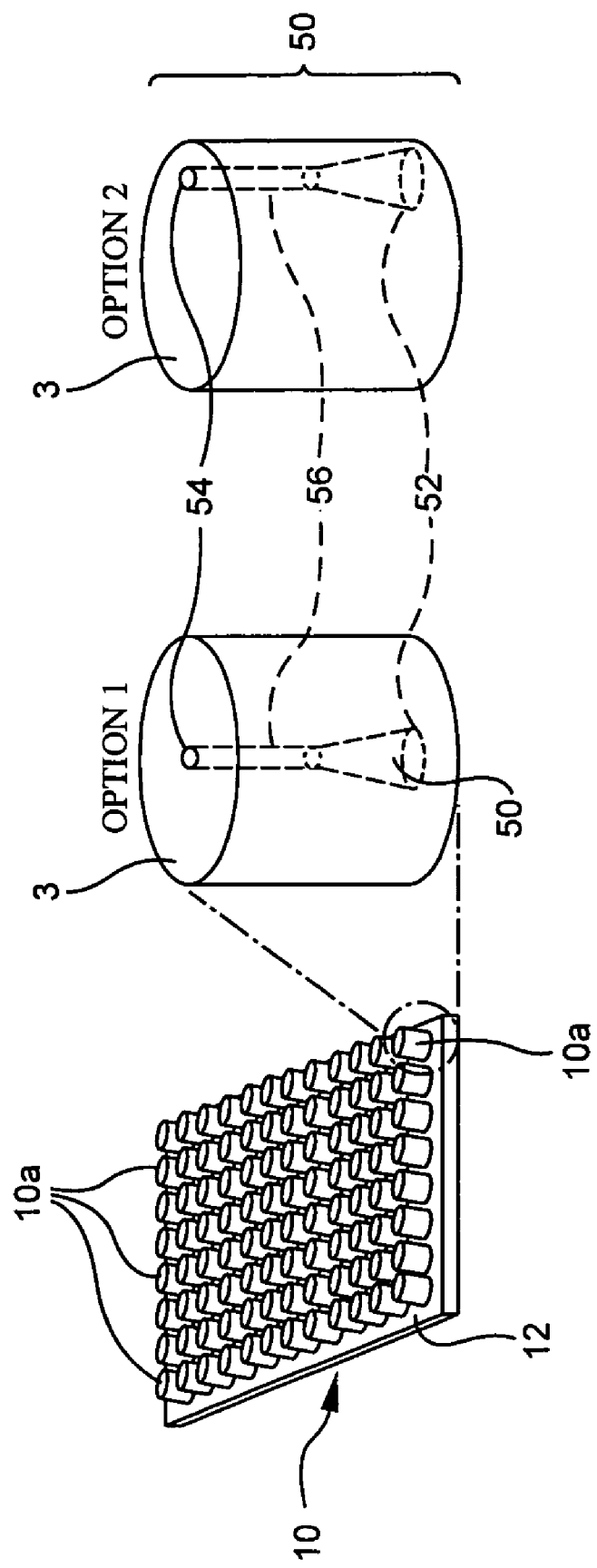
FIG. 14 shows a schematic representation of a hollow microcolumn plate with inlet and outlet ports, and a microchannel for sample transport and mixing. For illustration purposes, two different locations of the inlet and outlet are depicted.

In other embodiments, each microcolumn may have a shaft with an internal cavity. The cavity potentially can have a number of uses. According to one use, the present invention solves the evaporation and mixing problems in standard microplates without the need of additional wells. A hollow cavity 50, as FIG. 14 illustrates according to one conception, extends all the way through the microcolumn, from the support structure 12 to the remote first surface 3. The hollow cavity may be used as a conduit for introducing (e.g., by either pipette tip 57 or syringe needle) reagents or other fluids directly to the area of a micro-titer well located under the array of biosites on the surface of the microcolumn. Each hollow conduit 50 in the microcolumn will have an inlet 52, outlet 54, and a microchannel 56 of about 500 µm or less in diameter for transporting and mixing sample solution. FIG. 14 also shows two possible locations for the hollow conduit 50, either through the center or off to a side of the microcolumn. Each microcolumn may also have a number (e.g., 1-6) hollow conduits located around the periphery or at the center of the pillar. U.S. patent application Ser. No. 10/155540, incorporated herein by reference, describes in more detail, designs and uses of hollow conduits in a microcolumn.

Figure 15:
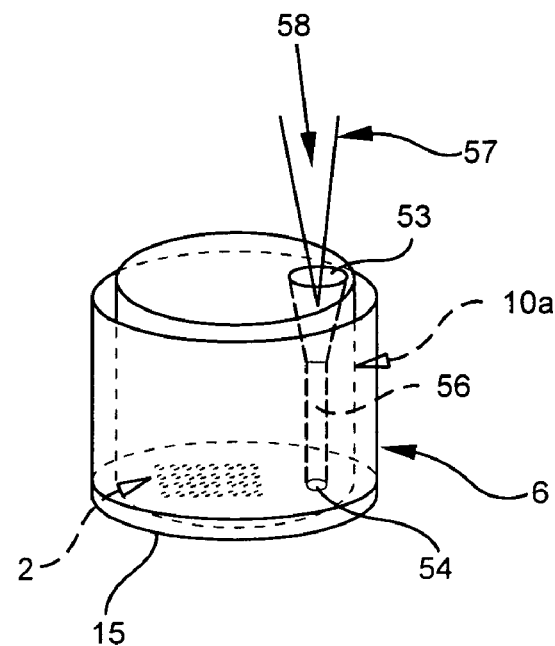
FIG. 15 illustrates the way a reaction sample can be injected through the hollow microcolumn plate into the wells of a micro-titer plate. Pipetting the sample up and down during incubation can promote microfluidic mixing.

For instance, according to the method detailed above, rectilinear arrays 2 of biological materials 1 are first deposited onto the first surface 3 of a microcolumn 10. When the microcolumn plate is inverted, first surface 3 faces downward and is inserted into a well 6 of a standard microplate. An assay mixture 58 is injected into the micro-titer well 6 through hollow conduit 50 in microcolumn 10, as shown in FIG. 15. Since each microcolumn effectively serves as a cover slip over all reagents or sample solution introduced into each well, the microcolumn minimizes evaporation from the well. The amount of assay mixture used can be adjusted by changing the distance (gap) between the surface printed with biological materials of each hollow pillar and the bottom of its corresponding micro-titer well. Due to the relatively close distance between the micropillar's first surface and the bottom of the well, surface tension or hydrostatic forces confine assay liquids to the area under the arrayed biological materials. This feature not only reduces the volume of reagents required to perform an assay, but localizes the use of reagent solution directly on the biological materials, and may even stimulate microfluidic flow throughout the assay. According to one way, the assay mixture may be pipetted up and down to create a microvacuum or suction, which promotes microfluidic mixing during incubation.

Figure 16:
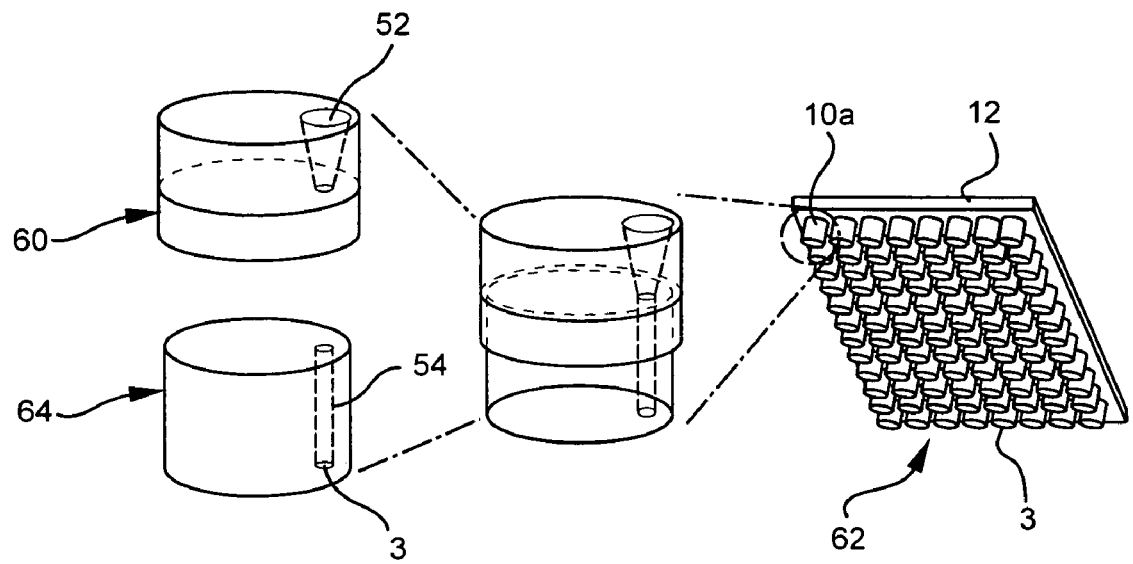
FIG. 16 shows a hollow microcolumn plate with exchangeable hollow pillar inserts of glass or polymer materials.

The microcolumn plate and hollow pillars can be made from glass or polymer or a combination of both. Preferably, glass hollow pillars are used in a microcolumn plate. As illustrated in FIG. 16, the device may comprise a polymer plate 62 with hollow polymer caps 60 can hold hollow glass pillars 64, which are inserted into the hollow polymer caps before use. The polymer plate 62 can be fabricated by injection molding techniques, and the hollow glass pillars can be fabricated by glass drawing technology. Also, the entire microcolumn plate, including the hollow pillars 10a, may be injection molded from polymer materials that do not themselves emit biofluorescence when imaged.

According to a second use, a hollow cavity may extend to just under the microcolumn's first surface, without breaking through. The cavity may extend possibly about 99.5% to 98.5% or less of the length of the microcolumn shaft. Into this cavity, sensors and detector devices such as optical fiber can be placed. Such sensors would allow one to visualize or detect with greater sensitivity the biological samples attached to the other side of the first surface of the microcolumn. Obviously, the microcolumn in such a situation would be necessarily made from a transparent material of high optical quality.

In a further embodiment, a microcolumn may be adapted to promote faster and easier extraction of magnetic beads that have biological material attached to them. A magnet of any shape or form and of a predetermined size and magnetic field strength is integrated into the design of the microcolumn. This design involves providing a magnet, such as of either a rod or disc-shape, inserting or molding integrally the magnet into the microcolumn. The magnet should be arranged such that the magnetic force is most concentrated at the effective end of the microcolumn—namely the first surface and its peripheral second surfaces—which will be inserted into a well of a multiwell plate. The ability to bind many metallic or magnetic beads laden with biologicals at once, without need for aspirating liquid solution from reaction vessels, greatly reduces the turn over time and increases overall high throughput of biological assays.

The device of the present is relative easy to manufacture. Both microcolumns and their support structure can be fabricated from a number of different materials. As mentioned before, these materials can be inorganic, such as glass or quartz, fused silica, ceramic, or metal; or, they can be organic like polymers or copolymers such as polypropylene, polystyrene, nylon membrane, etc, or a composite material. It can also have a metal surface like chromium, gold, platinum, or silicon. A microcolumn can be injection molded using polymeric or co-polymeric materials—such as polypropylene, polystyrene, polyethylene, etc—into microcolumn forms that have a relatively smooth first surface.

Glass microcolumns could be either molded as an integrally part of the support substrate, such as by a vapor deposition technique, or cut from glass dowels (e.g., borosilicate, boroaluminosilicate, or aluminosilicate glasses, fused silica or other high silicate-content (>85 wt. %) glasses), quartz, silicon, or ceramic materials, by a more mechanical process, and mounted onto a planar substrate of compatible material.

After the initial forming, further chemical modification of the first, second, or other surfaces of the microcolumns or any other portion or combination thereof, could be employed to achieve desired bio-reactive and bio-compatible properties. The top surface of a molded microcolumn can be modified with functional groups such as a coating of amino, carboxyl, hydroxyl, or anhydride groups, etc., which would permit biological molecules such as peptides, proteins, lipids, DNA, cell components, etc. to be immobilized by either covalent chemistry or non-covalent, electrostatic bonding. This coating may be either formed in situ on the substrate or later applied to the substrate.

For polymer materials, copolymers with reactive functional groups can also be used to mold microcolumns. For example, using poly(styrene-co-maleic anhydride) (SMA) produces a surface containing a reactive anhydride group to which molecules containing primary amino or hydroxyl groups can be attached by covalent means.

For glass substrates, on the other hand, the first surface of a glass microcolumn may be chemically modified with an organic coating. Samples of the desired biological materials are then printed or otherwise deposited in arrays onto the first surface of each microcolumn using, for example, either contact-pin printing or inkjet printing methods. For instance, glass surfaces can be modified with silane treatment. Substrates modified with gama-amino propyltrimethoxysilane (GAPS) permits DNA molecules to attach in the fabrication of DNA arrays.

The first surface of each microcolumn may comprise a thin metallic film or coating. Many kinds of metals can be vapor deposited onto either a plastic or glass surface to form a thin metallic layer. Possible metal films include aluminum, chromium, titanium, tantalum, nickel, zinc, lead, iron, copper, magnesium, manganese, cadmium, tungsten, cobalt, stainless steel, and alloys or oxides thereof. In a preferred embodiment, the metal surface is coated with a noble metal film, including of platinum, gold, or silver. In a particularly preferred embodiment, the coating comprises gold or a gold alloy. Electron-beam evaporation may be used to provide a thin coating of gold on the surface of the microcolumn. The gold metal film may be from about 60 nm to about 500 nm in thickness. In another embodiment, the metal film is about 1 nm to about 1 μm in thickness. Biological molecules, like membranes of lipids and/or proteins, nuceleic acids, ligands, etc., can attach to gold surfaces and form self-assembled monolayers (SAMs). Metal-coated microcolumns are also useful for mass spectrometry. As discussed above, making the microcolumn compatible with MALDI/TOF mass spectrometry instruments permits label-free detection of a variety of molecules such as proteins or protein/peptide fragments, DNA, RNA, and other small organic compounds.

The method of fabricating micropins would depend on the actual desired size and use. By way of illustration, a number of proprietary methods developed by Corning Incorporated for fabricating micropins are discussed below, but other methods known in the art which can accomplish the same result are also included in the scope of this disclosure. One example of making polymer micropins is by injection molding for inexpensive disposable embodiments. Each micropin is from about 10 microns to about 250 microns across, depending on the particular uses and needs for the array. Preferably, each micropin are on the order of about 50 microns to about 200 microns in diameter. Biological molecules are adhered to the tops of the micropins in a manner similar to that used for preparing microarray print-heads, such as described in detail in U.S. Pat. No. 6,051,190, issued to Birch et al. and the contents of which are incorporated herein by reference. According to the Birch '190 patent, a tool having at least one rod or pin-like structure is employed to transfer small amounts of liquid containing biological or chemical materials. Each rod on the tool has a wettable surface and at least a second surface that is non-wettable. The rod is immersed into a reservoir containing a liquid, for a predetermined period of time and at a predetermined depth. When the rod is removed from the reservoir a drop of liquid is retained on a wettable end of the rod. Very fine silica micropins could be produced by a second, alternate approach, which comprises using a reactive ion etching (RIE) process. With the RIE process, micropins can be made with a size ranging from of about 1 micron to about 400 microns across (diameter), but preferably about 50 microns or to about 250 microns, depending on the actual use for the array. According to the RIE process, a polished silica wafer, coated with a thick layer of a photoresist is imaged and developed and then etched either with or without an inductively-coupled plasma. The shape in the images of the photoresist mask (e.g., circle, square, triangle, polygon, etc.) defines the shape of the pin. The RIE process is discussed in detail in U.S. patent application Ser. No. 09/962,831, entitled "Pin Plate for Use in Array Printing and Method for Making the Pin Plate," by Michael B. Brady et al., also assigned to Corning Incorporated, and incorporated herein by reference.

Other techniques include traditional manufacturing processes such as using a photomask to expose selected areas of a photosensitive glass to ultraviolet light. The exposed areas are then etched with hydrofluoric acid to form the micropins. Or, an example includes making master pin plate image in a photoresist material and casting a silicone replica of the master pin plate.

In yet another embodiment, the present invention provides a biosensor device formed from microcolumns, coated with a waveguide and embossed with gratings, to enable real-time interaction analysis in a label free format. This embodiment can potentially overcome the fundamental limitations of current biosensor devices, in particular the relatively low-throughput processing of samples. Although micro-titer well plates offer higher throughput, they are not easily amenable to monitoring real-time interactions because fluidics for continuous flow is not available currently. Thus, deduction of kinetic parameters ($k_{on}$ ($M^{-1}s^{-1}$), $k_{off}$ ($s^{-1}$) from real-time measurements is difficult and prone to error because of mass-transport-limited binding and lateral steric effects. (See, Lahiri et al., Langmuir, 1999, 15, 7186-7198).

The biosensor device can be fabricated on microcolumns by various means. A preferred means is by thermoplastic processing. Thermoplastic processing involves using elevated temperatures and pressures to plastically deform a softened polymer. Most of the time, these extreme conditions require that the molds and tools used be made of steel. Lithography (e.g. e-beam lithography and UV-lithography) and direct writing (laser) techniques are commonly used to pattern grating structures onto glass and silicon substrates. While subsequent microreplication techniques could be used to generate metallic substrates bearing the micropattern for gratings. Direct patterning onto steel substrates greatly simplifies the process.

Patterning of sub-wavelength gratings, for instance, involves using an electron beam to write into a sensitive resist. This work has been mostly done onto glass-like surfaces, but it is proposed here to perform the operation on a tool-steel surface. In this case, the metallic surface is coated with the e-beam-sensitive resist, and grating lines can be written in the resist and corresponding areas of the steel substrate would be exposed. At this point, two avenues can be followed. First, new metal can be deposited inside the exposed areas; thus, building the grating lines up. Or, second, the metal can be selectively removed. In other words, the patterned resist can be used as an etch mask; thus, the grating lines will be built under the resist by etching away metal from adjacent exposed area. This can be applied when patterning monolithic tools or individual inserts.

A metallic bottom plate carrying the desired gratings pattern can be aligned and stacked together with a plate containing a number of holes. Polymer material is forced into the holes where it replicates the gratings pattern. When polymer hardens, the microcolumn is extracted from the mold. Each microcolumn bears on the face of its first surface a replica of the grating. According to a so-called monolithic approach, the bottom plate and associated microcolumn array can be made in a single piece. Then again, the device can consist of a carrier plate into which individual pattern-bearing plugs are inserted, analogous to the concept depicted in FIG. 16. This second configuration is called a modular approach, and it presents an advantage of allowing individual grating areas of the tool to be replaced in case those areas become damaged.

A method for using a microcolumn-based biosensor according to the invention, may comprise the following steps. First, immerse microcolumns, having immobilized biological probes on their first surfaces, in solutions of target moieties, contained in each well of a microplate, until stable signals ($S_{eq}$) corresponding to equilibrium are observed. Real-time measurements at this association phase would be used only to monitor the achievement of equilibrium and not to infer kinetics. A plot of $S_{eq}/C$ versus $S_{eq}$ would yield a slope equal to $1/K_d$, wherein C is the concentration of the probe solutions and $K_d$ ($=k_{off}/k_{on}$) is the equilibrium dissociation constant. Then, immerse the microcolumns in baths with continuous flow of flashing or washing buffers and monitor in real time the drop in the signal due to dissociation. There could be, for example, one bath for each microcolumn, or one large bath for the entire array of microcolumns. Since rebinding could cause artifacts in measurement of $k_{off}$, soluable targets in excess could be added to the washing buffer to capture dissociated probes. Infinite dilution of the probes is readily achievable, and enables convenient and accurate measurements of $k_{off}$. This method has several advantages, including a more accurate, indirect measurement of $k_{on}$ ($K_d^{-1}/k_{off}$).

For biochemical or cell assays, microcolumns may be used according to an embodiment in which microcolumn-immobilized chemical or drug molecules are inserted over cells cultured on the bottom of microplates. The drug molecules, for instance, are then released either actively if bound by covalent attachment (e.g., bonds cleaved by light exposed through a photomask) or passively if bound by non-covalent attachment (e.g., simple diffusion) into the assay reaction. Drug molecules, for instance, free in the medium will migrate and bind with a target on the cells.

The present invention also relates to a kit or assembly suitable for performing a biological assay. The assembly suitable for performing a biological or chemical assay, may comprise: an article having (a) a support structure, (b) a plurality of microcolumns projecting away from said support structure, (c) each of said microcolumns having a first surface remote from said support structure and at least a second surface; a micro-titer plate having a corresponding number of wells into which each of the microcolumns may be inserted; and a plurality of different biological materials immobilized on either: 1) the first surface of each microcolumn; 2) on an interior surface (e.g., bottom surface) of each well; or 3) both.

Each well in the micro-titer plate has a spacer located around the periphery of the bottom wall of the well, wherein the spacer maintains a capillary space between the bottom of the well and the first surface of the microcolumn. In another embodiment, the micro-titer well has a bottom wall 30 that is treated to be both hydrophobic 44, along the periphery near where the bottom wall meets the sidewall 40, and hydrophilic 46 in the center area of the bottom wall. This feature is illustrated in FIGS. 10A, 10B, and 10C. An aqueous reagent 48 is added to the well of FIG. 10A, where it is contained within the hydrophilic region at the center of the well bottom, seen in FIG. 10B. FIG. 10C is a three-dimensional perspective view of the situation in FIG. 10B, and shows the liquid reagent 48 confined to the area immediately underneath the biological array 2 on the microcolumn 10, which enables optimized reagent and array contact. The assembly may further comprise a second tray for performing common washes, and/or a physical adaptor for holding the microcolumns when imaging either the arrays or biological analytes attached thereto.

The present microcolumn array design has many advantages over arrays printed deep on the bottom of micro-titer plate wells. Just to point out but a few of the more important benefits—first, the new design affords researchers a simpler means for manipulating and processing multiple samples in a single device. For instance, to perform washing steps in current micro-titer plates, normally one needs to do much pipetting and suctioning of liquids into and out of each individual micro-titer well. This is a tedious task to perform. With microcolumns there is no such need. Unlike conventional micro-titer plate arrays, one merely withdraws the microcolumns from their reaction wells and reinserts them into different individual wash wells or a common wash reservoir, which simplifies the washing step. Since the microcolumn is designed to work with micro-titer plates, all preparation, reaction, and even reading steps of a typical assay can be conducted on a single device.

Second, microcolumns can be agitating to mix the assay solution reagents for more efficient reaction kinetics. This feature generates microfluid currents and increases the interaction and dispersion of probe and target molecules, leading to a faster reaction speed. Since the first of a microcolumn can be brought very close to the bottom of a micro-titer well, one need not have much liquid volume. One can use smaller amounts of fluid and samples, which saves both cost and materials.

A third advantageous feature of the microcolumn design is the relatively large and flat microcolumn first surface, which provides a level plane for reading samples. Biological samples are located on a relatively exposed, raised surface, which is better for imaging and easier detection by a CCD camera or laser scanner, unlike some of the hinderances associated with micro-titer plates.

It is envisioned that the present invention is a simple and elegant solution for a variety of applications to provide increased throughput. An array of microcolumns, each having multiple biological samples deposited on its first surface, can well address the increasing demand in biological pharmaceutical or research, as well as medical and clinical applications, for assays with high-volume throughput of different biological samples, while simultaneously, increasing imaging sensitivity. Instead of biological materials deposited on the constrained bottoms of micro-titer wells and the associated difficulties of arranging the materials there, microcolumns enable researchers to print an array of many, different biological samples of interest on each open first surface in a rectilinear arrangement, like that of microarrays. Parallel analysis of multiple different samples on the same array device, such as for screening multiple patient samples for the same phenotype, could be performed more easily and quickly.

EXAMPLES

Example 1

To validate the concept of a microcolumn-based array platform, DNA microarray hybridization experiments were performed on glass microcolumns. The first surface of each glass microcolumn was polished and treated with a gama-amino propyl-trimethyl-silane (GAPS) coating. To compare glass slide and microcolumn formats, parallel microarray hybridization experiments were done on current GAPS-treated slides. Ten different PCR fragments, as indicated in Table 1, below, representing ten human genes were printed on glass microcolumns and on GAPS-coated slides using a Cartesian pin printer. The Cy3 and Cy5-cDNA probe ratios in hybridization mix was 1×=14 ng.

TABLE 1

| Number | Gene | Cy5-labeled Probe | Cy3-labeled Probe |
|--------|------|-------------------|-------------------|
| 1 | AATK | 50x | 1x |
| 2 | ABCD | 50x | 1x |
| 3 | ACTB | 10x | 1x |
| 4 | ADH2 | 10x | 1x |
| 5 | AMPH | 5x | 1x |
| 6 | ANXA5 | 5x | 1x |
| 7 | AOC3 | 1x | 1x |
| 8 | API4 | 1x | 1x |
| 9 | BAD | 0x | 1x |
| 10 | BCL2A | 0x | 1x |

Table 2 summarizes the telative location of each of the PCR fragments on the microcolumn and slide.

TABLE 2

| Genes Printed on Arrays Key to location of numbered Gene Samples on Arrays | | | |
|---|---|---|---|
| 1 | 4 | 7 | 10 |
| 1 | 4 | 7 | 10 |
| 2 | 5 | 8 | |
| 2 | 5 | 8 | |
| 3 | 6 | 9 | |
| 3 | 6 | 9 | |

On these two array formats, hybridizations using Cyanine5- and Cyanine3-labeled cDNA probes were performed in parallel. To evaluate the dynamic range of hybridization detection, hybridizations were done using fixed amounts of Cy5-labeled cDNA probes for each gene and a titration of Cy3-labeled cDNA probe for each gene. The hybridization protocol was as follows: 1) Prehybridization: incubated slide and microcolumn arrays in 2×SSC/0.05% SDS/0.2% BSA 10 min. at 42° C., 1×SSC 2 min at RT, and three times in 0.2×SSC 2 min at RT; 2) Hybridization: 75 µL hybridization solutions were used; 3) Washing: the arrays were washed twice in 2×SSC/0.05% SDS 5 min at 42° C., twice in 1×SSC 5 min at RT, and three times in 0.2×SSC at RT. For the slide, the solution was placed on the slide over the array and covered by a cover-slip. For the microcolumn array, the solution was placed in a well of a 96-well plate and the microcolumn was inserted into the well with the array on the first surface of the microcolumn submerged in the solution. The arrays were incubated in this manner at 42° C. overnight. The arrays were then dried and scanned using a GenePix scanner.

Figure 11A:
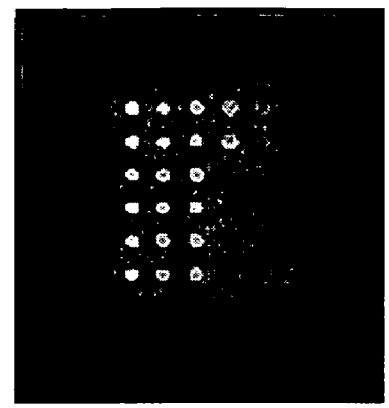
FIG. 11A is an image of a conventional slide-based array.
Figure 11B:
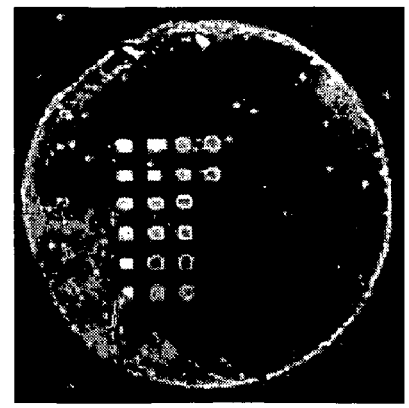
FIG. 11B is an image that shows a set of biological samples on first of a microcolumn. The samples were developed in parallel and under the same conditions as the slide-based array in FIG. 11A.

The hybridization results obtained from the slide-based array, in FIG. 11A, were comparable to those obtained from the array printed on the microcolumn in FIG. 11B. FIGS. 11A and 11B are scanned-images of cDNA hybridizations performed on a GAPS-treated slide and a glass microcolumn, respectively. The sensitivity and quality of hybridization on the GAPS slide and microcolumn are virtually indistinguishable. These results substantiate the feasibility of using the microcolumn plate platform for array assays.

Figure 12A:
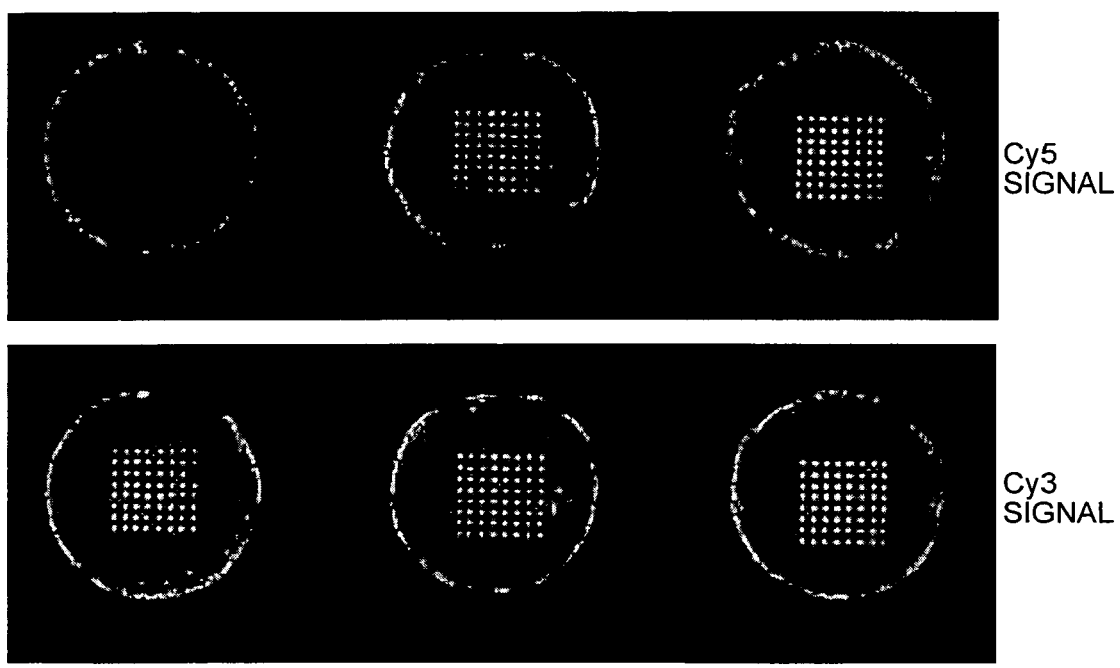
FIG. 12A shows images under pseudo-coloration of three experiments conducted under three different conditions using an embodiment of the present invention.

To demonstrate that microcolumn devices can be used to perform parallel array assays using different hybridization conditions, three identical arrays were printed onto three GAPS-treated glass microcolumns attached to a common glass support. These arrays comprised an 8×8 pattern of a 1.5 kB PCR fragment of the human β-actin gene printed onto each microcolumn. Cy3- and Cy5-labeled -actin PCR fragments were used as probes. Hybridizations were performed using a fixed amount of Cy3-labeled β-actin probe for each microcolumn (250 ng) and varying amounts of Cy5-labeled β-actin probe among the microcolumns (5, 25, and 100 ng), as indicated in FIG. 12A. Parallel hybridizations were performed in three wells of a 1×8-Stripwell plate (Corning®) by inserting the array device into the wells and submerging the microcolumns in the fifty microliter hybridization solutions. Hybridization conditions were similar to the example above except that the incubation time was one hour. Following the wash steps, the microcolumn arrays were scanned with the GenePix scanner using the adaptor device shown in FIG. 9. The resulting scanned image of the three microcolumns is shown in FIG. 12A.

TABLE 3

|  | Microcolumn #1 | Microcolumn #2 | Microcolumn #3 |
| --- | --- | --- | --- |
| Cy3-labeled probe (ng) | 250 | 250 | 250 |
| Cy5-labeled probe (ng) | 5 | 25 | 100 |

Figure 12B:
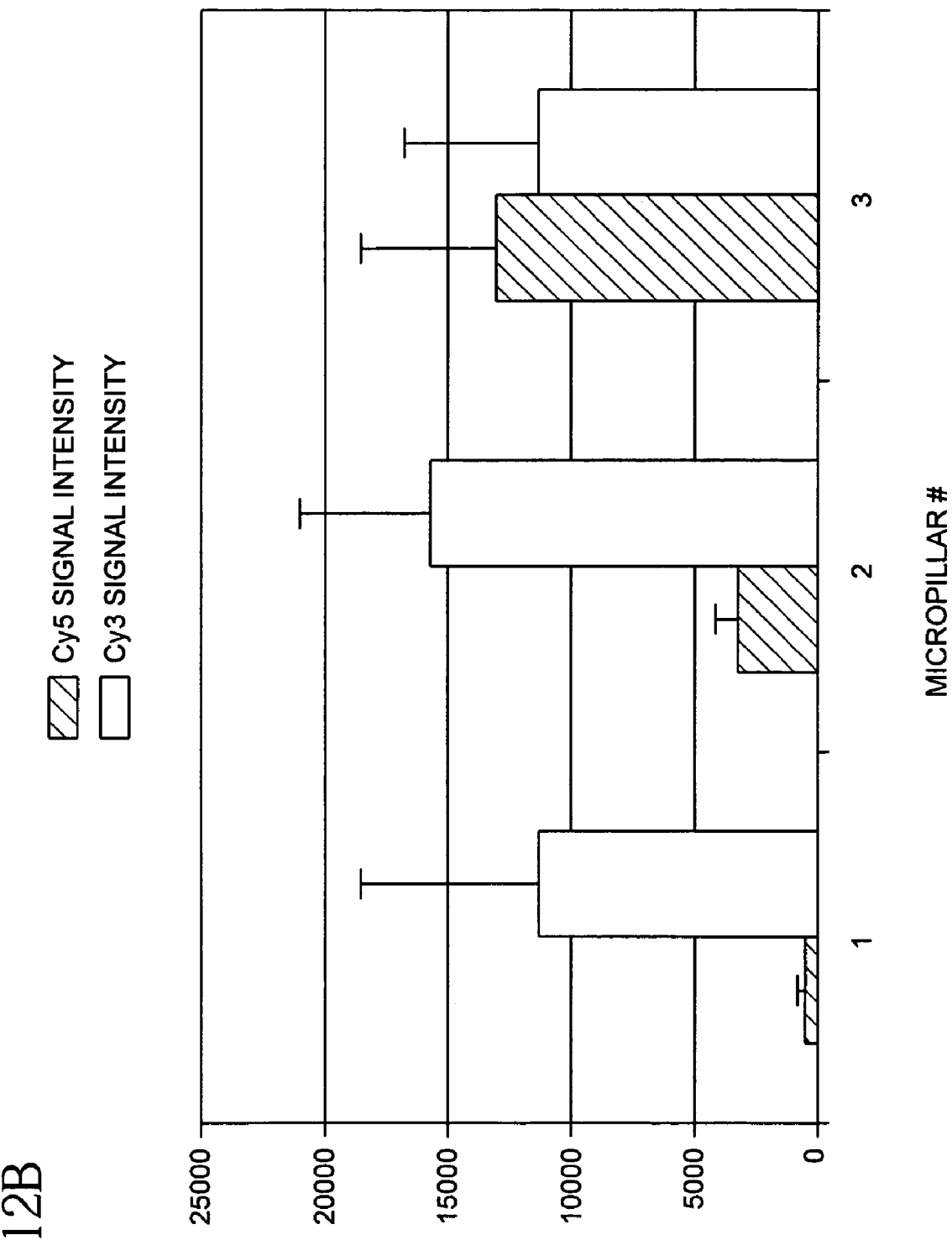
FIG. 12B is a bar graph of average signal intensity for the multiple biosites on the three microcolumns used in the three experiments of FIG. 12A.

To compare the levels of Cy3- and Cy5-probe hybridizations on each microcolumn, the Cy3 and Cy5 signal intensities of the 64 biosites on each microcolumn were averaged. As shown in FIG. 12B, the average Cy5 signal intensity steadily increased from microcolumn #1 to #2, and from microcolumn #2 to #3, while the Cy3 signal intensity remained constant, reflective of the Cy5 and Cy3 probes conditions used in the hybridization. Thus, three different hybridization conditions were successfully assayed in parallel using the microcolumn device, demonstrating its utility as a high throughput assay tool.

Example 2

Use of the present microcolumn device in conjunction with a multiwell plate has at least two significant advantages. The advantages include the ability to minimize assay volumes and to increase assay sensitivity. Both of these features are related to the relatively small volume of the gap formed between the bottom surface of the well and the first surface of the microcolumn. For example, glass microcolumns according to the present invention, when inserted into corresponding silicone chambers (Vivascience, flexiPERM micro 12) having a GAPS-coated glass slide attached as the bottom surface of the chambers, forms a 175 μm gap between the opposing surfaces of the slide and the microcolumn. A small volume of solution is all that is required to fill the gap. A number of cDNA arrays, each with twenty-five gene spots, were printed on the GAPS-coated slides at locations corresponding to the chamber wells. Tables 4 and 5, respectively, summarize the identity and location of each gene on a slide. Labeled probes, as described above, were generated with RNA from control as well as Mitomycin C-treated HepG2 cells. In each labeling reaction, about 2 μg of total RNA was used. The resulting Cy3 and Cy5-labeled probes were used in a 30 μL hybridization reaction (=1× probe concentration in 30 μL). To test the efficacy of assay with reduced solution volumes and increased probe concentrations, Applicants ran four tests, the conditions of which are summarized in Table 4. First, a control assay without microcolumn was conducted using 1× probe concentration in 30 μl of hybridization mixture. A second assay used 1× probe concentration in a reduced volume of 9 μl hybridization mixture. In a third and fourth assay, Applicants inserted a microcolumn into the well. The third assay used 1× probe concentration in 9 μl of hybridization. The fourth assay used 3× probe concentration in 9 μl of hybridization

TABLE 4

| Assay | Probe concentration | Volume (μL) | Microcolumn Inserted |
| --- | --- | --- | --- |
| 1 | 1× | 30 | No |
| 2 | 1× | 9 | No |
| 3 | 1× | 9 | Yes |
| 4 | 3× | 9 | Yes |

Probes of cDNA were placed the hybridization solution onto the arrays within each well. After 4 hours at 42° C., the arrays were washed and scanned.

Figure 17A:
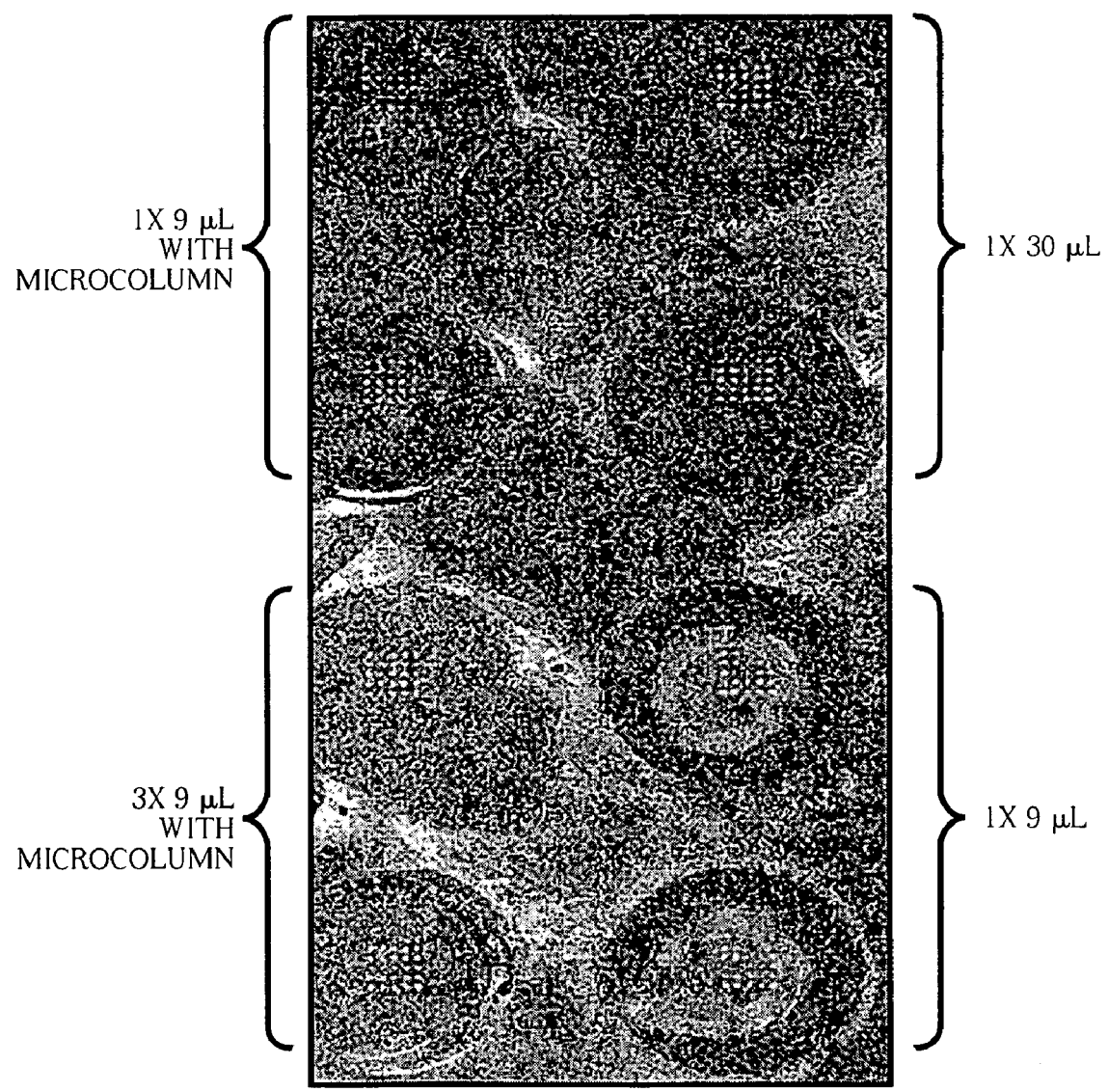
FIG. 17A shows an image of biological arrays.
Figure 17B:
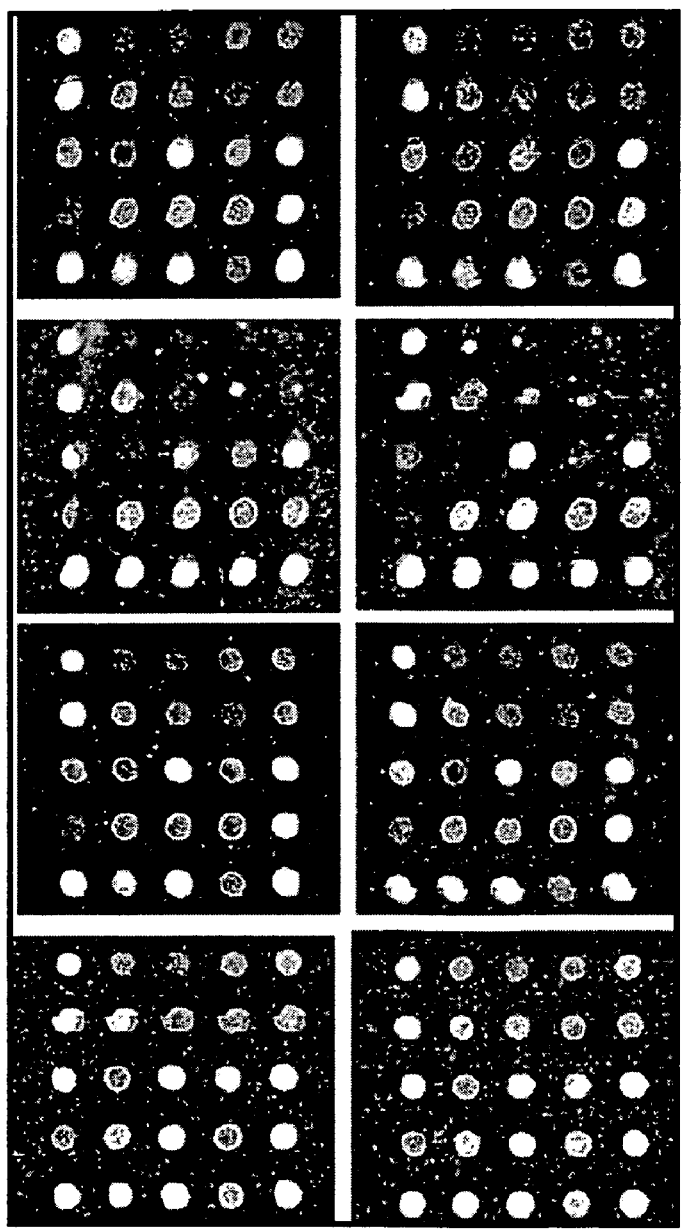
FIG. 17B shows an enlarged view of the individual biological arrays of FIG. 17A.
Figure 18A:
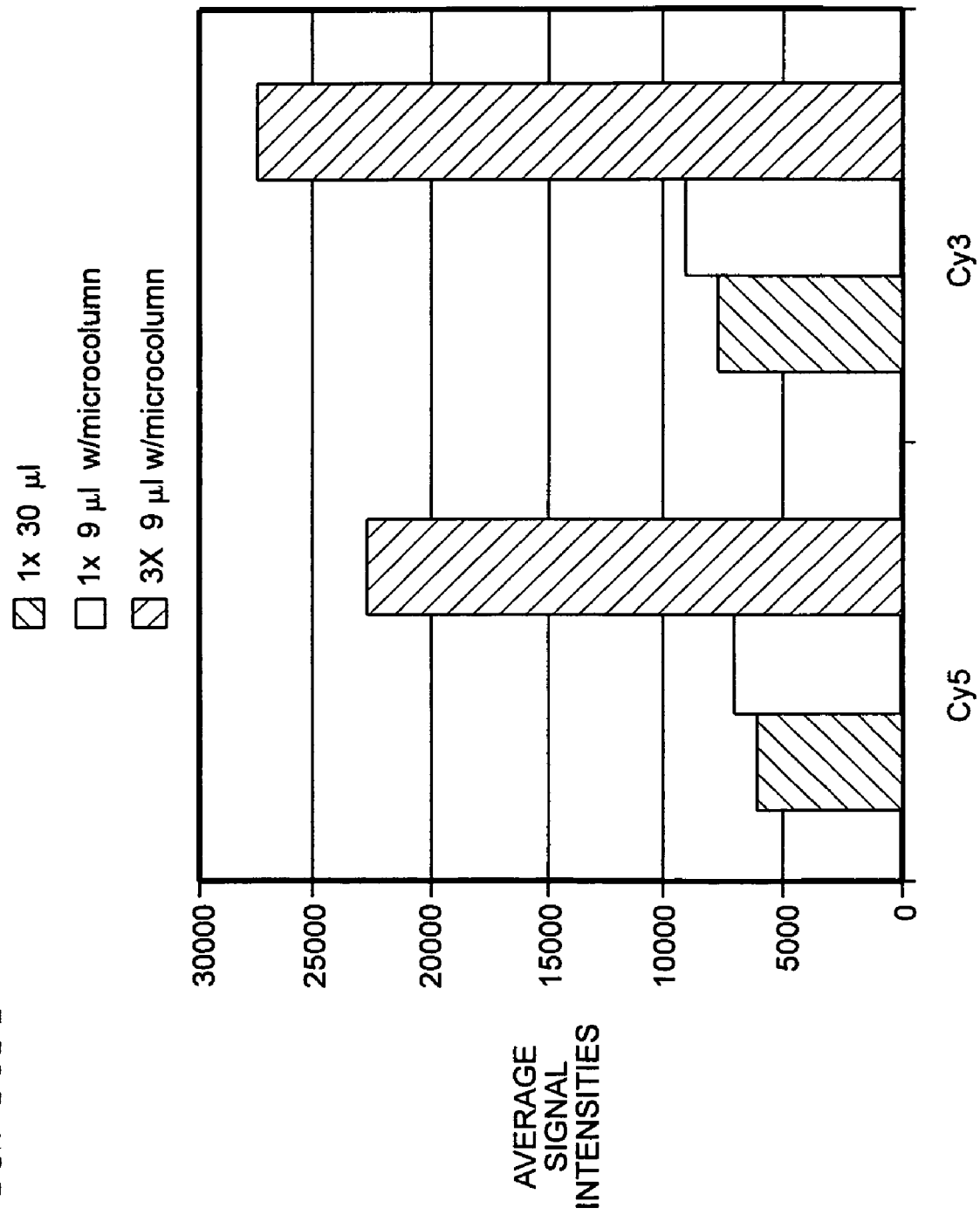
FIGS. 18A-E are graphs that show quantitative analysis of the arrays in FIGS. 17A and 17B.
Figure 18B:
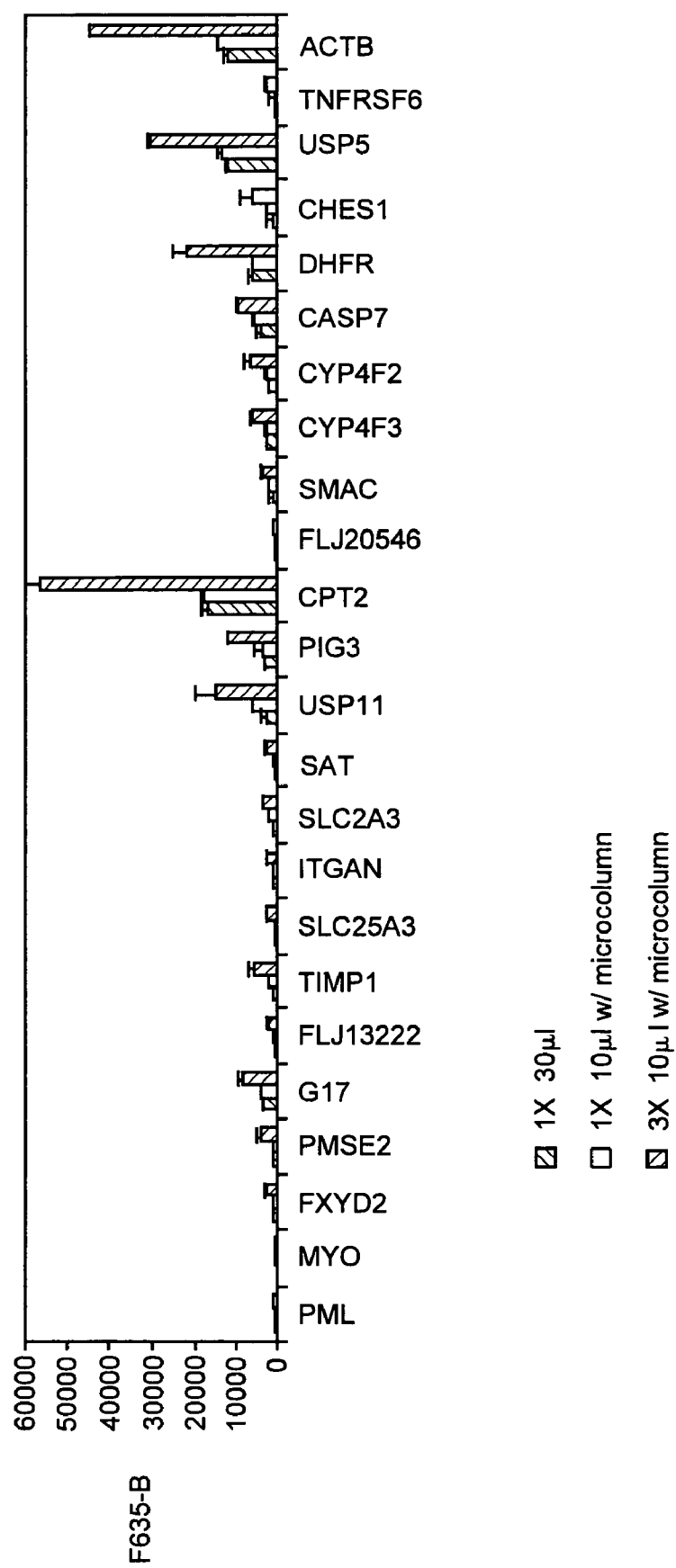
Figure 18C:
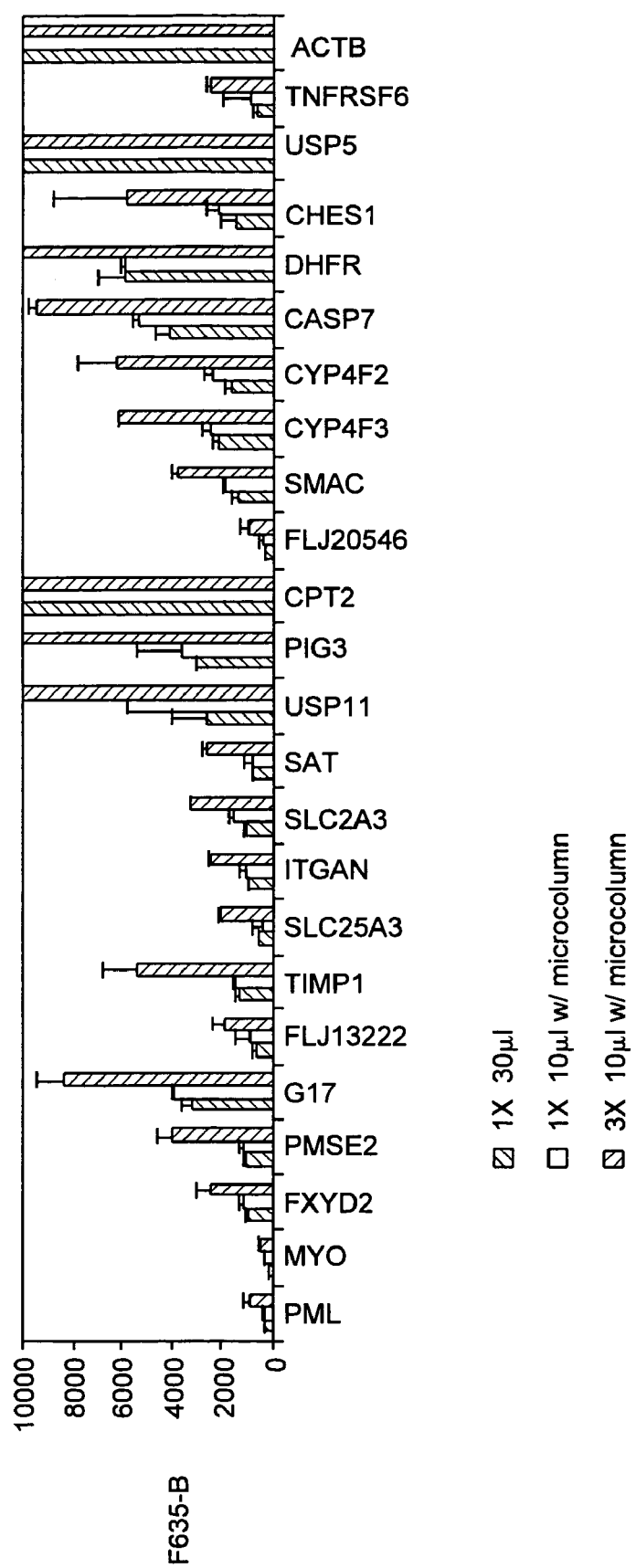
Figure 18D:
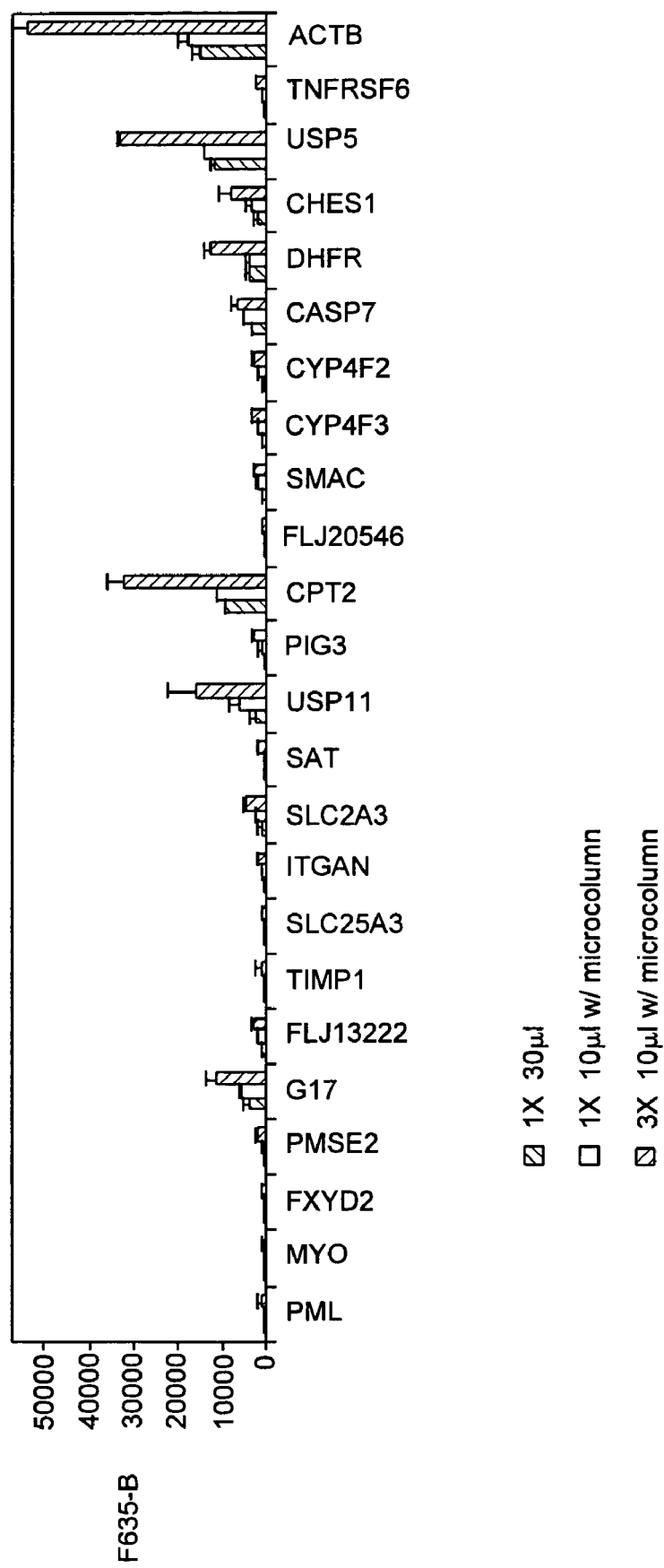
Figure 18E:
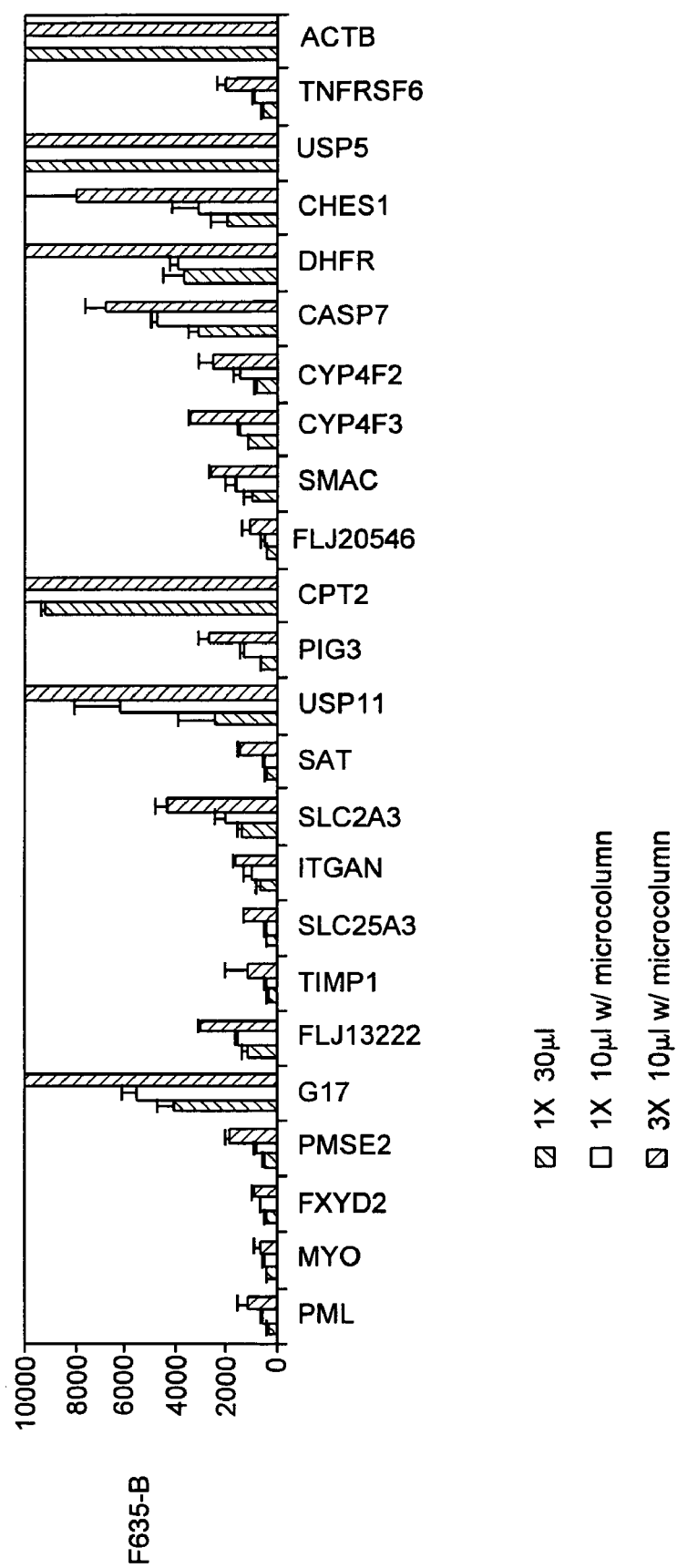

FIGS. 17A and 17B shows images of the arrays on the surface of the glass slide. FIG. 17B shows the biological arrays under magnification. As presented on the upper four arrays of FIG. 7B, hybridization was preformed without a microcolumn to serve as a cover slip in assays 1 (30 μL 1×) and 2 (9 μL 1×). In assays 3 (9 μL 1×) and 4 (9 μL 3×), the lower four arrays of FIG. 7B were each covered with a microcolumn.

FIGS. 18A-E shows a series of graphs which summarize the results of the hybridization experiments. In FIG. 15A, quantitative analysis of the hybridization data reveals that even though assay 3 used a much lower amount (9 μL) of hybridization solution, it produced essentially equivalent hybridization signals as found with assay 1 (30 μL) using the same probe concentration. The presence of the column device in assay 3 prevented evaporation and enhanced hybridization kinetics. Hybridizations in assay 2, which used a reduced volume without a column, dried up during the incubation. Thus, even using an assay volume of 3-times less than conventional amounts, an assay having a microcolumn as a cover can hybridize effectively with comparable hybridization signals. Furthermore, in assay 4, where the same absolute amount of probe was used in a smaller volume, the comparable average signal intensity for both Cy3 and Cy5 labels were more than 3.5 times higher than that observed in conventional assay 1. This phenomenon is due presumably to the increased probe concentration. Hence, a microcolumn device will help generate higher hybridization signals in assays where the probe amount is limited, such as in high throughput 96-microplate array assays.

TABLE 5

Genes used in the array printed on the slide.

| Position | Gene |
|---|---|
| 1 | Control |
| 2 | PML |
| 3 | MYO |
| 4 | FXYD2 |
| 5 | PMSE2 |
| 6 | G17 |
| 7 | FLJ13222 |
| 8 | TIMP1 |
| 9 | SLC25A3 |
| 10 | ITGAN |
| 11 | SLC2A3 |
| 12 | SAT |
| 13 | USP11 |
| 14 | PIG3 |
| 15 | CPT2 |
| 16 | FLJ20546 |
| 17 | SMAC |
| 18 | CYP4F3 |
| 19 | CYP4F2 |
| 20 | CASP7 |
| 21 | DHFR |
| 22 | CHES1 |
| 23 | USP5 |
| 24 | TNFRSF6 |
| 25 | ACTB |

Table 6 shows the relative location of each of the genes of Table 5 in the array on the slide.

TABLE 6

| 1 | 2 | 3 | 4 | 5 |
|---|---|---|---|---|
| 6 | 7 | 8 | 9 | 10 |
| 11 | 12 | 13 | 14 | 15 |
| 16 | 17 | 18 | 19 | 20 |
| 21 | 22 | 23 | 24 | 25 |

Example 3

Figure 13A:
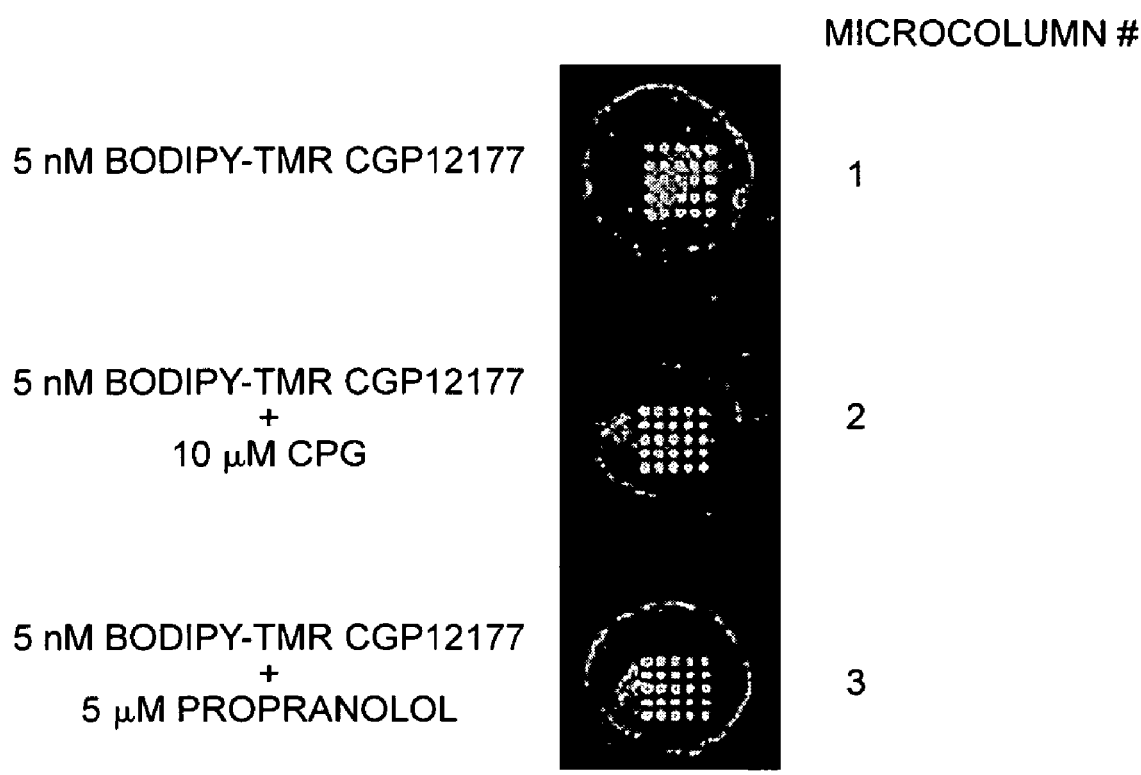
FIG. 13A shows images under pseudo-coloration of a high-throughput experiment of ligand-binding assays for G-protein coupled receptor (GPCR) applications performed using an embodiment of the present invention.
Figure 13B:
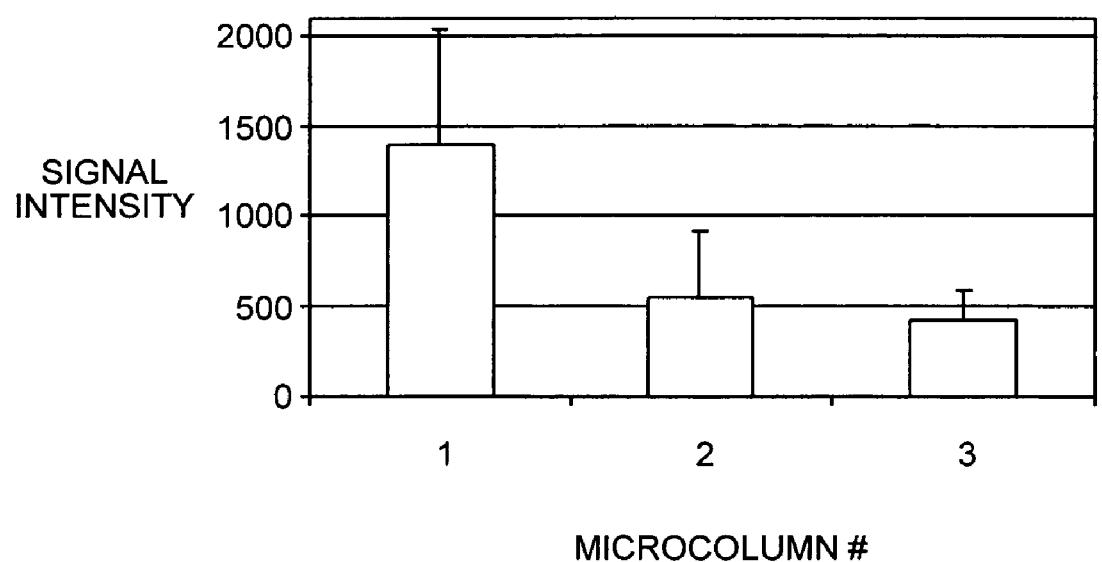
FIG. 13B is a bar graph of average signal intensity of the experimental results of FIG. 13A.

Further uses for the present microcolumn device include G-protein coupled receptor (GPCR) applications. Arrays of adrenergic $\beta_1$ receptor (Biosignal Packard) were prepared on membranes and printed onto three adjacent microcolumns—using a robotic pin printer in a fashion like that described in U.S. patent application Ser. No. 09/854,786, "Arrays of Biological Membranes and Methods and Use Thereof," by Lahiri et al., which is incorporated herein by reference. These glass microcolumns were coated with a thin gold layer and functionalized with GAPS. The particular description about the chemical preparation, deposition, and reaction of functionalized gold coatings is detailed also in U.S. patent application Ser. No. 09/854,786. Functionalized gold surfaces have been shown to yield signal-to-noise ratios that are far superior to ordinary, uncoated glass surfaces. To assay ligand binding, the microcolumns were inserted into the wells of an 1×8-Stripwell plate (Corning®) containing a fluorescently-labeled $\beta_1$ receptor ligand (bodipy-TMR CGP12177) (5 nM) in a ligand binding buffer (50 mM Tris-HCl, 2 mM EDTA, 1 mM $MgCl_2$, pH 7.4, 0.1% BSA). To verify the binding specificity of the bodipy-TMR CGP12177, competition experiments were performed on the second and third microcolumns by co-incubating with excess unlabeled ligands (10 µM CPG for microcolumn #2 and 10 µM propranolol (a $\beta_1$ antagonist) for microcolumn #3). Following incubation of about one hour, the microcolumns were removed, washed, and scanned to assess ligand binding on the array. Binding of bodipy-TMR CGP12177 to the $\beta_1$ receptor was seen by high fluorescent signal on the array printed on microcolumn #1. Co-incubation with excess unlabeled ligands (microcolumns #2 and #3) greatly decreased the fluorescent signal, indicating binding specificity. Results of these assays are shown in FIGS. 13A and 13B. The experiments demonstrate that one can perform feasibly high throughput ligand binding assays on receptor arrays printed on microcolumns.

Although the present invention has been described by way of examples, those skilled in the art will understand that the invention is not limited to the embodiments specifically disclosed, and that various modifications and variations can be made without departing from the spirit and scope of the invention. Therefore, unless changes otherwise depart from the scope of the invention as defined by the following claims, they should be construed as included herein.

We claim:

1. A product for performing biological or chemical analysis, selected from the group consisting of hybridization of nucleic acids, assays of chemical molecules peptides, proteins, lipids, membranes, and viral particles, and cell transfection and reverse cell transfection, the product comprising:
   a) a support structure;
   b) a number of microcolumns projecting away from said support structure;
   c) each microcolumn having a first surface remote from said support structure and at least a second surface; and
   d) an array of multiple samples of biological material deposited on each first surface;
   e) wherein, each microcolumn is sized to fit within a corresponding well of a microtiter plate and wherein said microcolumn has a hollow cavity extending from said support structure, through said microcolumn, to said first surface.

2. The product according to claim 1, wherein said hollow cavity comprises an inlet port, an outlet port, and a microchannel connecting the inlet and outlet ports.

3. The product according to claim 2, wherein said microchannel has a diameter of about 500 µm or less.

4. The product according to claim 1, wherein said microcolumn has a hollow cavity that extends about 99.5% or less through the length of a shaft of said microcolumn and is capable of receiving a fiber optical imaging component.

5. The product according to claim 1, wherein each of said microcolumns further comprises either:
   1) a hydrophilic wetting surface, and at least a hydrophobic non-wetting second surface, or
   2) a roughened surface that entraps fluids with multiple fluid contact angles, and having a different biological material attached to each of said wetting surface or said roughened surface.

6. The product according to claim 1, wherein said microcolumns have a cross section dimension generally between about 4 mm and about 1 µm.

7. The product according to claim 1, wherein said microcolumns are made of a material selected from a glass, polymeric, metallic, ceramic, or composite material.

8. An comprising:
a) a support structure;
b) a plurality of microcolumns, each extending orthogonally away from a surface of said support structure;
c) each microcolumn having a first surface and at least a second surface; and
d) a plurality of micropins located on said first surface of each microcolumn;
e) wherein each micropin has a surface with a different biological material attached thereto, to form an organized array of multiple biological materials on said first surface of each microcolumn, and
wherein each micropin has either 1) a hydrophilic wetting surface and at least one non-wetting second surface, or 2) a roughened surface that entraps fluids with multiple fluid contact angles.

9. The product according to claim 8, wherein said microcolumns have a cross-sectional dimension in the range from about 0.5 mm to about 5.0 mm.

10. The product according to claim 8, wherein said microcolumns has a hollow cavity extending from said support structure, through said microcolumn, to said first surface.

11. The product according to claim 10, wherein said hollow conduit comprises an inlet port, an outlet port, and a microchannel connecting the inlet and outlet ports.

12. The product according to claim 11, wherein said microchannel has a diameter of about 500 μm or less.

13. The product according to claim 8, wherein each of said microcolumns has a hollow cavity that extends about 99.5% or less through the length of a shaft of said microcolumn and is capable of receiving a fiber optical imaging component.

14. An product comprising: a support structure; at least one microcolumn projecting away from a planar surface of said support structure; said microcolumn having a first surface remote from said support structure and at least a second surface; and a sheet of multiple, different biological material arranged in a plurality of containment spaces defined by a lattice-like network located on said first surface.

15. The product according to claim 14, wherein said biological material is arranged in a rectilinear array within said network of containment spaces.

16. The product according to claim 14, wherein a number of said microcolumns is organized in an array that has a footprint that corresponds to a micro-titer plate.

17. The product according to claim 14, wherein said biological material comprises: DNA, RNA, oligonucleotides, plasmids, peptides, proteins; lipids, membranes, chemical molecules, pharmaceutical compounds, viral particles, cells, sub-cellular components, and cellular products.

18. The product according to claim 14, wherein said microcolumn is made of a material selected from a glass, polymeric, metallic, ceramic, or composite material.

19. The product according to claim 14, wherein said first surface has a material selected from group consisting of an amino-propylsilane-treated glass, quartz, fused silica, polypropylene, polystyrene, nylon filter, gold, platinum, chromium, and silicon.

20. The product according to claim 14, wherein said microcolumn has a hollow cavity extending from said support structure, through said microcolumn, to said first surface.

21. The product according to claim 20, wherein said hollow conduit comprises an inlet port, an outlet port, and a microchannel connecting the inlet and outlet ports.

22. The product according to claim 21, wherein said microchannel has a diameter of about 500 μm or less.

* * * * *

UNITED STATES PATENT AND TRADEMARK OFFICE
CERTIFICATE OF CORRECTION

PATENT NO.        : 7,332,328 B2                                              Page 1 of 1
APPLICATION NO.   : 10/236120
DATED             : February 19, 2008
INVENTOR(S)       : Michael Donavon Brady et al.

It is certified that error appears in the above-identified patent and that said Letters Patent is hereby corrected as shown below:

*Col.*   *Line*
23       1       "8. An comprising:" should be replaced with --8. A product comprising:--
23       34      "14. An product comprising: a support structure; at least" should be replaced with --A product comprising: a support structure; at least--

Signed and Sealed this

Eighth Day of July, 2008

JON W. DUDAS
*Director of the United States Patent and Trademark Office*